(12) United States Patent
Myung et al.

(10) Patent No.: US 7,909,867 B2
(45) Date of Patent: *Mar. 22, 2011

(54) INTERPENETRATING POLYMER NETWORK HYDROGEL CORNEAL PROSTHESIS

(75) Inventors: David Myung, Santa Clara, CA (US); Christopher Ta, Saratoga, CA (US); Curtis W. Frank, Cupertino, CA (US); Won-Gun Koh, Kyunggi Yongin (KR); Jaan Noolandi, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/639,049

(22) Filed: Dec. 13, 2006

(65) Prior Publication Data

US 2007/0179605 A1 Aug. 2, 2007

Related U.S. Application Data

(63) Continuation-in-part of application No. 11/243,952, filed on Oct. 4, 2005, and a continuation-in-part of application No. 11/409,218, filed on Apr. 20, 2006, now abandoned, which is a continuation-in-part of application No. 11/243,952, filed on Oct. 4, 2005.

(60) Provisional application No. 60/843,942, filed on Sep. 11, 2006, provisional application No. 60/616,262, filed on Oct. 5, 2004, provisional application No. 60/673,172, filed on Apr. 20, 2005, provisional application No. 60/673,600, filed on Apr. 21, 2005.

(51) Int. Cl.
*A61F 2/14* (2006.01)

(52) U.S. Cl. ...... 623/5.16; 623/6.56; 424/427; 523/106; 351/160 H

(58) Field of Classification Search .................. 623/5.16, 623/6.56; 424/427; 351/160 H; 435/180, 435/396; 525/903; 523/106
See application file for complete search history.

(56) References Cited

U.S. PATENT DOCUMENTS 4,678,468 A * 7/1987 Hiroyoshi .................... 623/1.49
(Continued)

FOREIGN PATENT DOCUMENTS

WO WO 94/01468 A1 * 1/1994
(Continued)

OTHER PUBLICATIONS

European search report for European Application No. 05807352.9 dated Mar. 30, 2010.*
(Continued)

*Primary Examiner* — Paul Prebilic
(74) *Attorney, Agent, or Firm* — Lumen Patent Firm

(57) ABSTRACT

The present invention provides materials that have high glucose and oxygen permeability, strength, water content, and resistance to protein adsorption. The materials include an interpenetrating polymer network (IPN) hydrogel that is coated with biomolecules. The IPN hydrogels include two interpenetrating polymer networks. The first polymer network is based on a hydrophilic telechelic macromonomer. The second polymer network is based on a hydrophilic monomer. The hydrophilic monomer is polymerized and cross-linked to form the second polymer network in the presence of the first polymer network. In a preferred embodiment, the hydrophilic telechelic macromonomer is PEG-diacrylate or PEG-dimethacrylate and the hydrophilic monomer is an acrylic-based monomer. Any biomolecules may be linked to the IPN hydrogels, but are preferably biomolecules that support the growth of cornea-derived cells. The material is designed to serve as a corneal prosthesis.

41 Claims, 20 Drawing Sheets

U.S. PATENT DOCUMENTS

| | | | |
|---|---|---|---|
| 4,680,336 A | | 7/1987 | Larsen et al. |
| 4,693,715 A | | 9/1987 | Abel, Jr. |
| 4,931,287 A | * | 6/1990 | Bae et al. .................. 424/484 |
| 4,973,493 A | * | 11/1990 | Guire .......................... 427/2.24 |
| 4,978,352 A | | 12/1990 | Fedorov et al. |
| 5,030,230 A | | 7/1991 | White |
| 5,067,961 A | | 11/1991 | Kelman et al. |
| 5,112,350 A | | 5/1992 | Civerchia et al. |
| 5,171,318 A | | 12/1992 | Gibson et al. |
| 5,374,515 A | | 12/1994 | Parenteau et al. |
| 5,580,929 A | | 12/1996 | Tanaka et al. |
| 5,644,049 A | * | 7/1997 | Giusti et al. .................. 536/53 |
| 5,674,942 A | * | 10/1997 | Hill et al. .................. 525/131 |
| 5,716,633 A | | 2/1998 | Civerchia |
| 5,836,313 A | | 11/1998 | Perez et al. |
| 5,904,927 A | * | 5/1999 | Amiji .......................... 424/422 |
| 5,962,005 A | | 10/1999 | Saga et al. |
| 5,976,648 A | | 11/1999 | Li et al. |
| 6,005,160 A | | 12/1999 | Hsiue et al. |
| 6,160,084 A | * | 12/2000 | Langer et al. ................ 528/272 |
| 6,224,893 B1 | * | 5/2001 | Langer et al. ................ 424/423 |
| 6,254,637 B1 | | 7/2001 | Lee et al. |
| 6,372,815 B1 | * | 4/2002 | Sulc et al. .................. 523/106 |
| 6,388,043 B1 | * | 5/2002 | Langer et al. .................. 528/80 |
| 6,391,055 B1 | | 5/2002 | Ikada et al. |
| 6,645,715 B1 | | 11/2003 | Griffith et al. |
| 6,673,112 B2 | | 1/2004 | Nigam |
| 6,689,165 B2 | | 2/2004 | Jacobs et al. |
| 6,726,322 B2 | | 4/2004 | Andino et al. |
| 6,866,936 B2 | | 3/2005 | Opolski |
| RE38,839 E | | 10/2005 | Magnante |
| 7,279,507 B2 | * | 10/2007 | Hu et al. .................. 523/108 |
| 2002/0007217 A1 | | 1/2002 | Jacob et al. |
| 2002/0198280 A1 | * | 12/2002 | Baba et al. .................. 522/99 |
| 2004/0049268 A1 | | 3/2004 | Noolandi et al. |
| 2005/0147685 A1 | | 7/2005 | Osada et al. |
| 2007/0005140 A1 | * | 1/2007 | Kim et al. .................. 623/17.16 |
| 2007/0068816 A1 | * | 3/2007 | Solomon et al. ............. 204/606 |
| 2008/0119930 A1 | * | 5/2008 | Osada et al. .................. 623/14.12 |
| 2008/0317818 A1 | * | 12/2008 | Griffith et al. ............... 424/427 |

FOREIGN PATENT DOCUMENTS

| | | | |
|---|---|---|---|
| WO | WO 00/02937 A1 | * | 1/2000 |
| WO | WO 03/093337 A1 | * | 4/2003 |
| WO | WO 2004/055057 A1 | * | 7/2004 |

OTHER PUBLICATIONS

Gong et al. "Double-Network Hydrogels with Extremely High Mechanical Strength" (2003) Adv. Materials No. 14 pp. 1155-1158.

Cruise, G.M., D.S. Scharp and J.A. Hubbell, Characterization of permeability and network structure of interfacially photopolymerized poly(ethylene glycol) diacrylate hydrogels. Biomaterials, 1998. 19(14): p. 1287-94.

Padmavathi, N.C. and P.R. Chatterji, Structural characterization and swelling behavior of poly (ethylene glycol) diacrylate hydrogels. Macromolecules, 1996. 29: p. 1976-1979.

Merrett, K., C.M. Griffith, Y. Deslandes, G. Pleizier, and H. Sheardown, Adhesion of corneal epithelial cells to cell adhesion peptide modified pHEMA surfaces. J Biomater Sci Polym Ed, 2001. 12(6): p. 647-71.

Houseman, B.T. and M. Mrksich, The microenvironment of immobilized Arg-Gly-Asp peptides is an important determinant of cell adhesion. Biomaterials, 2001. 22(9): p. 943-55.

Hern, D.L. and J.A. Hubbell, Incorporation of adhesion peptides into nonadhesive hydrogels useful for tissue resurfacing. J Biomed Mater Res, 1998. 39(2): p. 266-76.

Matsuda, T., K. Inoue and T. Sugawara, Development of micropatterning technology for cultured cells. ASAIO Transactions, 1990. 36(3): p. M559-62.

Tsuk, A.G., V. Trinkaus-Randall and H.M. Leibowitz, Advances in polyvinyl alcohol hydrogel keratoprostheses: protection against ultraviolet light and fabrication by a molding process. Journal of Biomedical Materials Research, 1997. 34(3): p. 299-304.

Carlsson, D.J., F. Li, S. Shimmura, and M. Griffith, Bioengineered corneas: how close are we? Curr Opin Ophthalmol, 2003. 14(4): p. 192-7.

Evans, M.D., G.A. McFarland, R.Z. Xie, S. Taylor, J.S. Wilkie, and H. Chaouk, The use of corneal organ culture in biocompatibility studies. Biomaterials, 2002. 23(5): p. 1359-67.

Mann, B.K., A.S. Gobin, A.T. Tsai, R.H. Schmedlen, and J.L. West, Smooth muscle cell growth in photopolymerized hydrogels with cell adhesive and proteolytically degradable domains: synthetic ECM analogs for tissue engineering. Biomaterials, 2001. 22: p. 3045-3051.

Gong et al. Double-Network Hydrogels with Extremely High Mechanical Strength. Adv. Materials 15 (14) 1155-1158, 2003.

Hern et al. Incorporation of adhesion peptides into nonadhesive hydrogels useful for tissue resurfacing. J. Biomed. Materials Research 39(1) 266-276, 1998.

Evans et al. The use of corneal organ culture in biocompatibility studies. Biomaterials 23 1359-1367, 2002.

* cited by examiner

INTERPENETRATING POLYMER NETWORK HYDROGEL CORNEAL PROSTHESIS

CROSS-REFERENCE TO RELATED APPLICATIONS

This application claims priority from U.S. Provisional Patent Application No. 60/843,942, filed Sep. 11, 2006, which is incorporated herein by reference. This application is a continuation-in part of U.S. patent application Ser. No. 11/243,952, filed Oct. 4, 2005, which claims priority from U.S. Provisional Patent Application No. 60/616,262, filed Oct. 5, 2004, and from U.S. Provisional Patent Application No. 60/673,172, filed Apr. 20, 2005, all of which are incorporated by reference herein. This application is also a continuation-in-part of U.S. Application Ser. No. 11/409,218, filed Apr. 20, 2006, now abandoned, which claims priority from U.S. Provisional Patent Application No. 60/673,600, filed Apr. 21, 2005, and which is a continuation-in-part of U.S. patent application Ser. No. 11/243,952, filed Oct. 4, 2005, which claims priority from U.S. Provisional Patent Application No. 60/616,262, filed Oct. 5, 2004, and from U.S. Provisional Patent Application No. 60/673,172, filed Apr. 20, 2005, all of which are incorporated by reference herein.

FIELD OF THE INVENTION

The present invention relates generally to corneal implants. More particularly, the present invention relates to an interpenetrating network hydrogel material useful as a corneal prosthesis.

BACKGROUND

It is estimated that there are 10 million people worldwide who are blind due to corneal diseases (See e.g. Carlsson et al. (2003) in a paper entitled "*Bioengineered corneas: how close are we?*" and published in "*Curr. Opin. Ophthalmol.* 14(4): 192-197"). Most of these will remain blind due to limitations of human corneal transplantation. The major barriers for treating these patients are corneal tissue availability and resources, particularly for people in developing countries. To have corneas available for transplantation, a system of harvesting and preserving them must be in place. This requires locating potential donors, harvesting the tissue within several hours of death, preserving the tissue, and shipping it to the appropriate facility within one week. Patients who have had refractive surgery may not be used as donors. Therefore, a shortage of corneas may occur in the future, even in developed countries, as the number of patients undergoing refractive surgery increases. Even among patients who are fortunate enough to receive a corneal transplant, a significant number will develop complications that will result in the loss of vision. The most common complications are graft rejection and failure and irregular or severe astigmatism. In successful cases, the improvement in vision may take many months following the surgery due to graft edema and astigmatism.

A biocompatible artificial cornea with tissue integration and epithelialization can replace the need for a human cornea and provide excellent surgical outcomes. Such an artificial cornea can eliminate the risk of corneal graft rejection and failure, as well as astigmatism, and enable rapid visual recovery. An artificial cornea will ensure an unlimited supply for transplantation anywhere in the world, without the resources required of an eye tissue bank, and eliminate the concern for human cornea shortages due to refractive surgery. Moreover, the technology developed for the artificial cornea can also be applied to the treatment of refractive errors, such as nearsightedness. Through a procedure known as epikeratoplasty (or corneal onlay), a thin polymer can be attached to the cornea to change the refractive index. A biocompatible epithelialized onlay placed over the cornea has an advantage over current technology of laser in situ keratomileusis (LASIK), which requires irreversible corneal tissue removal.

It would be desired to develop an artificial cornea that supports a stable epithelialized surface. Multilayered, stratified epithelial cells would serve as a protective barrier against infections and prevent destructive enzymes from gaining access to the device-cornea interface. The critical requirements for epithelial support of the device are a biocompatible surface for epithelial cellular adhesion and good permeability of glucose and nutrients through the device to support the adherent cells. Other important characteristics of an artificial cornea include optical clarity, biocompatibility, good mechanical strength, and the ability to integrate with stromal tissue.

Accordingly, it would be considered an advance in the art to develop an artificial cornea encompassing these desirable requirements or characteristics.

SUMMARY OF THE INVENTION

The present invention provides a material having high oxygen and nutrient permeability, strength, water content, and resistance to protein adsorption. The material includes an interpenetrating polymer network (IPN) hydrogel, as well as biomolecules covalently linked to the hydrogel. The IPN contains a first polymer network, which is based on a hydrophilic telechelic macromonomer, and a second polymer network, which is based on a hydrophilic monomer. The hydrophilic monomer is polymerized and cross-linked to form the second polymer network in the presence of the first polymer network. Preferably, the first polymer contains at least about 50% by dry weight of telechelic macromonomer, more preferably at least about 75% by dry weight of telechelic macromonomer, and most preferably at least about 95% by dry weight of telechelic macromonomer. The telechelic macromonomer preferably has a molecular weight of between about 575 Da and about 20,000 Da. Mixtures of molecular weights may also be used.

In a preferred embodiment, the telechelic macromonomer is poly(ethylene) glycol (PEG) diacrylate or poly(ethylene) glycol (PEG) dimethacrylate. Also preferably, the hydrophilic monomer forming the second network is acrylic acid, acrylamide, hydroxyethyl acrylamide, N-isopropylacrylamide, methacrylic acid, 2-acrylamido-2-methylpropanesulfonic acid, 2-hydroxyethyl methacrylate, 2-hydroxyethyl acrylate or derivatives thereof.

Any suitable biomolecules may be covalently linked to the IPN hydrogel. Preferably, the biomolecules are at least one of proteins, polypeptides, amino acids, carbohydrates, or nucleic acids. In a preferred embodiment, the material further includes corneal epithelial cells or other cornea-derived cells. In addition, at least one surface of the interpenetrating polymer network hydrogel may be surface modified with a layer of poly(ethylene) glycol (PEG) macromonomers, polymerized PEG macromonomers, polymerized PEG diacrylate, or polymerized PEG dimethacrylate.

In another embodiment, the interpenetrating polymer network hydrogel includes grafted polymers. For example, a hydrophilic monomer may be grafted onto the first polymer network, a telechelic macromonomer may be grafted onto the second polymer network, or both.

The material of the present invention has a number of desirable properties. These properties include high tensile strength (on the order of 1 MPa), high nutrient permeability (diffusion coefficient in the range of about $10^{-5}$ cm$^2$/sec to about $10^{-7}$ cm$^2$/sec), high water content (between about 70% and about 95%), and high transparency (at least about 70%). These properties make the material excellent for use in ophthalmic applications. In a preferred embodiment, the material is used as a corneal prosthesis, such as an artificial cornea, corneal implant, corneal onlay, or corneal inlay.

When the inventive material is used as an artificial cornea, it preferably includes a skirt peripheral to an IPN hydrogel core. This skirt is preferably hydrophilic, contains pores, is hydrogel-based, and is biocompatible. The skirt may be made of the same material as the core, or may be a different material. Preferably, the core and skirt are made from the same material and simultaneously. In another embodiment, the core and skirt are made from the same material but in sequential steps. In yet another embodiment, the skirt is made of poly(2-hydroxyethyl acrylate) (PHEA). Preferably (but not necessarily), the skirt also contains biomolecules covalently linked to it.

BRIEF DESCRIPTION OF THE FIGURES

The present invention together with its objectives and advantages will be understood by reading the following description in conjunction with the drawings, in which.

DETAILED DESCRIPTION OF THE INVENTION

Synthesis of Interpenetrating Polymer Network Hydrogels

The present invention provides materials made of interpenetrating polymer network (IPN) hydrogels with biomolecules covalently linked to the hydrogels. The new materials have properties making them desirable as biomaterials for use, e.g., in ophthalmic applications. The hydrogels are particularly well suited as a material for corneal prostheses, such as artificial corneas, corneal onlays, corneal inlays, and corneal implants.

Figure 1:
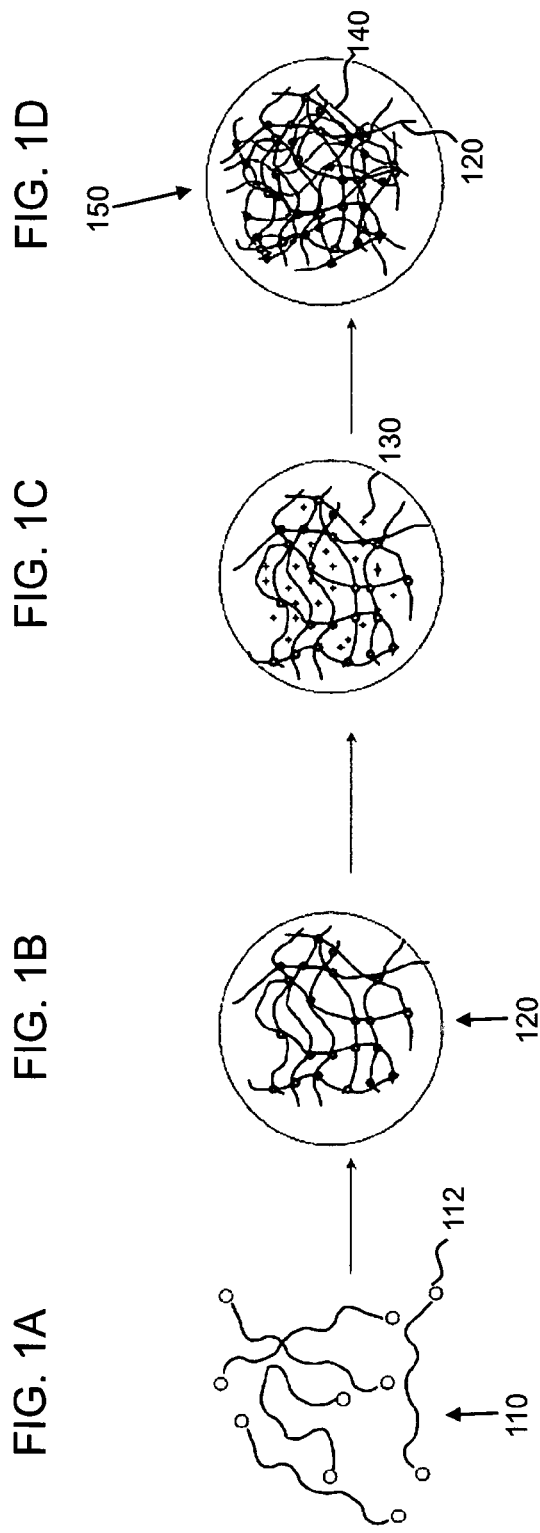
FIGS. 1A-D show the steps for synthesis of an interpenetrating polymer network hydrogel according to the present invention.

FIG. 1 shows the steps required for synthesis of an IPN hydrogel according to the present invention. The starting material for the hydrogel is a solution of telechelic macromonomers 110 with functional end groups 112. The telechelic macromonomers are polymerized to form a first polymer network 120. Next, hydrophilic monomers 130 are added to the first polymer network 120. Hydrophilic monomers 130 are then polymerized and cross-linked in the presence of first polymer network 130 to form second polymer network 140. This results in formation of an IPN hydrogel 150.

Any hydrophilic telechelic macromonomer may be used to form the first polymer network. In a preferred embodiment, polyethylene glycol (PEG) macromonomers are used as the basis of the first network. PEG is known to be biocompatible, soluble in aqueous solution, and can be synthesized to give a wide range of molecular weights and chemical structures. The hydroxyl end-groups of the bifunctional glycol can be modified into photo-crosslinkable acrylate or methacrylate end-groups, converting the PEG macromonomers to PEG-diacrylate (PEG-DA) or PEG-dimethacrylate (PEG-DMA) macromonomers. Adding a photoinitiator to a solution of PEG-diacrylate or PEG-dimethacrylate macromonomers in water and exposing the solution to UV light results in the crosslinking of the PEG-DA or PEG-DMA macromonomers, giving rise to a PEG-DA or PEG-DMA hydrogel. Polymerizing and crosslinking a second network inside the first network will give rise to the IPN structure. Preparing IPN hydrogels through free-radical polymerization has the additional advantage that it will enable the use of molds to form corneal prostheses of desired shape. The free-radical polymerization can be initiated through UV irradiation—in which case transparent molds can be used—or through other means such as thermal-initiation in which non-transparent molds can be used. Preferably, the first polymer network contains at least 50%, more preferably at least 75%, most preferably at least 95% of the telechelic macromonomer by dry weight.

Any hydrophilic monomer may be used to form the second polymer network according to the present invention. To optimize mechanical and other properties of the IPN hydrogel, a variety of acrylic based monomers may be used, such as acrylic acid, acrylamide, hydroxyethyl acrylamide, N-isopropylacrylamide, methacrylic acid, 2-acrylamido-2-methylpropanesulfonic acid, 2-hydroxyethyl methacrylate, 2-hydroxyethyl acrylate or derivatives thereof. In a preferred embodiment, poly(acrylic acid)(PAA) hydrogel is used as the second polymer network.

In a preferred embodiment, the IPN hydrogel is synthesized by a (two-step) sequential network formation technique based on UV initiated free radical polymerization. A precursor solution for the first network is made of purified PEG-DA or PEG-DMA dissolved in phosphate buffered saline (PBS) solution with, e.g., 2,2-dimethoxy-2-phenylacetophenone (DMPA) or 2-hydroxy-2-methyl-propiophenone as the UV sensitive free radical initiator. In other embodiments, the hydrogel can be synthesized by free radical polymerization initiated by other means, such as thermal-initiation and other chemistries not involving the use of ultraviolet light. In the case of UV polymerization, the precursor solution is cast in a transparent mold and reacted under a UV light source at room temperature. Upon exposure, the precursor solution undergoes a free-radical induced gelation and becomes insoluble in water. The mold is fabricated in such a way that yields hydrogels at equilibrium swelling with dimensions typical of corneal prostheses.

To incorporate the second network, the PEG-based hydrogels are removed from the mold and immersed in the second monomer solution, such as an aqueous solution of (10-100% v/v) acrylic acid containing a photo-initiator and a cross-linker, such as about 0.1% to 10% triethylene glycol dimethacrylate (TEGDMA), for 24 hours at room temperature. Other cross-linkers may be used, e.g. ethylene glycol dimethacrylate, ethylene glycol diacrylate, polyethylene glycol dimethacrylate, or polyethylene glycol diacrylate. The swollen gel is then exposed to the UV source and the second network is polymerized and crosslinked inside the first network to form an IPN structure. Other monomer candidates for the second network, such as acrylic acid derivatives, methacrylic acid and its derivatives, acrylamide, or 2-acrylamido-2-methylpropanesulfonic acid can be also incorporated into the PEG-based hydrogel using the same initiator, crosslinking agent and polymerization procedure. Preferably, the molar ratio of the first network macromonomer to the second network monomer ranges from about 1:1 to about 1:5000. Also preferably, the weight ratio of the first network to the second network is in the range of about 10:1 to about 1:10. All synthesized hydrogels can be stored in sterile aqueous conditions until further use.

In one embodiment of the present invention, UV light-absorbing monomers can be incorporated into the synthetic process by co-polymerization. In particular, a benzotriazole monomer (2-(2'methacryloxy-5'-methylphenyl)-benzotriazole (Polysciences, Inc., Warrington, Pa.) and a benzophenone monomer (2-hydroxy-4-acrylyloxyethoxy)-benzophenone (Cyasorb UV-2098, Cytec Industries, Inc., West Patterson, N.J.) can be used. These have been incorporated into (vinyl alcohol) hydrogels by Tsuk and coworkers (Tsuk et al. (1997) in a paper entitled "*Advances in polyvinyl alcohol hydrogel keratoprostheses: protection against ultraviolet light and fabrication by a molding process*" and published in "*J. Biomed. Mat. Res.* 34(3):299-304"). Once the UV-absorbing monomers have been incorporated into the materials, the light-absorbing capacity can be tested using a spectrophotometer. Finally, the refractive index of all candidate materials can be measured using an automated refractometer (CLR 12-70, Index Instruments, Cambridge, UK) or manually using an Abbe refractometer.

Figure 2:
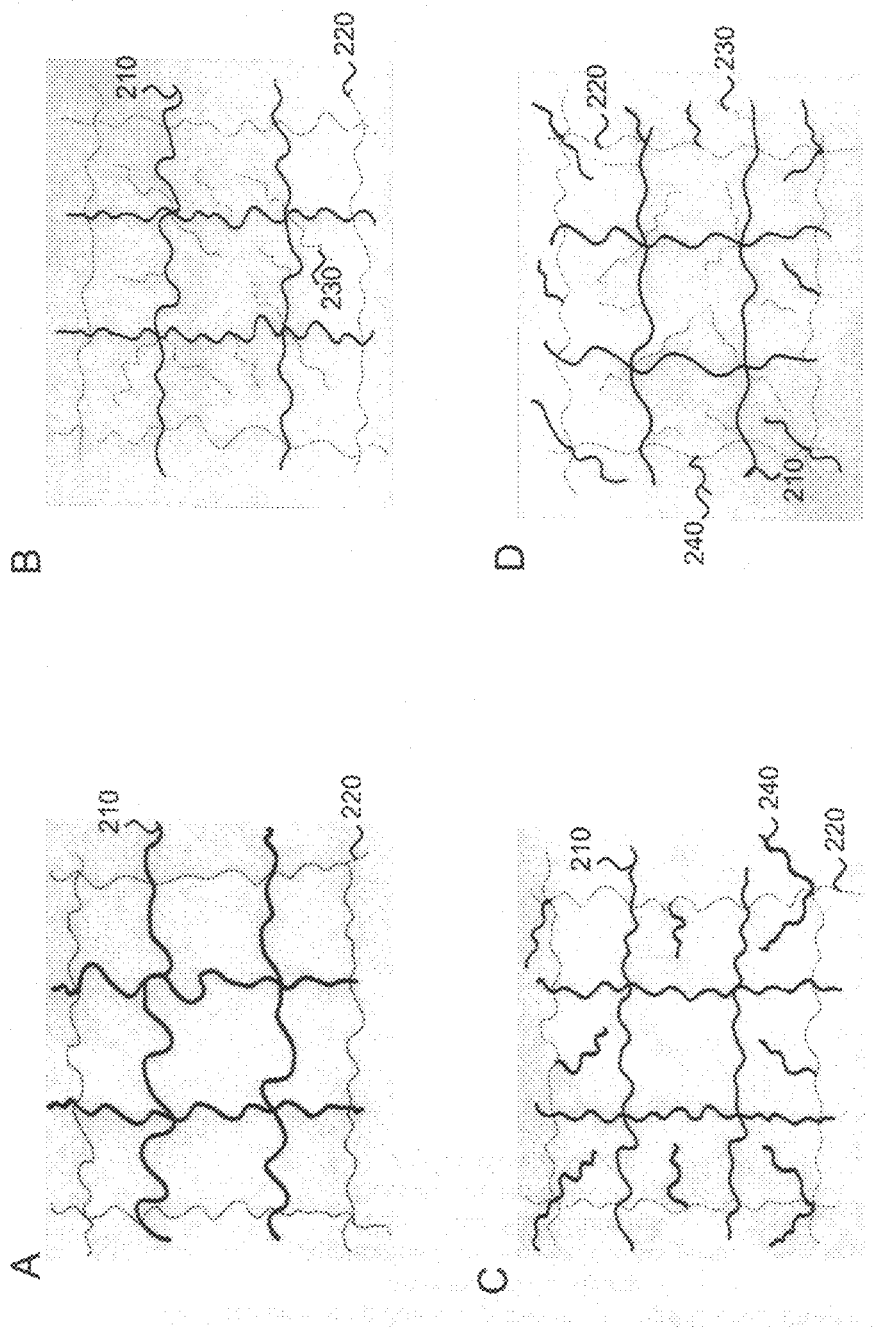
FIG. 2 shows grafted interpenetrating polymer network hydrogels according to the present invention.

In one embodiment of the present invention, grafted polymers are used to form the IPN. FIG. 2A shows a standard IPN according to the present invention, with first polymer network 210 and second polymer network 220. FIG. 2B shows an IPN in which first polymer network 210 is grafted with hydrophilic monomer 230. Hydrophilic monomer 230 may be, e.g., acrylic acid, acrylamide, hydroxyethyl acrylamide, N-isopropylacrylamide, methacrylic acid, 2-acrylamido-2-methylpropanesulfonic acid, 2-hydroxyethyl methacrylate, 2-hydroxyethyl acrylate or derivatives thereof. FIG. 2C shows an IPN in which second polymer network 220 is grafted with hydrophilic telechelic macromonomer 240. Hydrophilic telechelic macromonomer 240 may be, e.g., PEG-DA or PEG-DMA. FIG. 2D shows an IPN in which first polymer network 210 is grafted with hydrophilic monomer 230 and second polymer network 220 is grafted with hydrophilic telechelic macromonomer 240. The grafted networks are made by polymerizing aqueous mixtures of the two components in ratios that yield a network that is predominantly made from one polymer but has grafted chains of the second polymer.

Properties of Interpenetrating Network Hydrogels
Mechanical Strength

Figure 3:
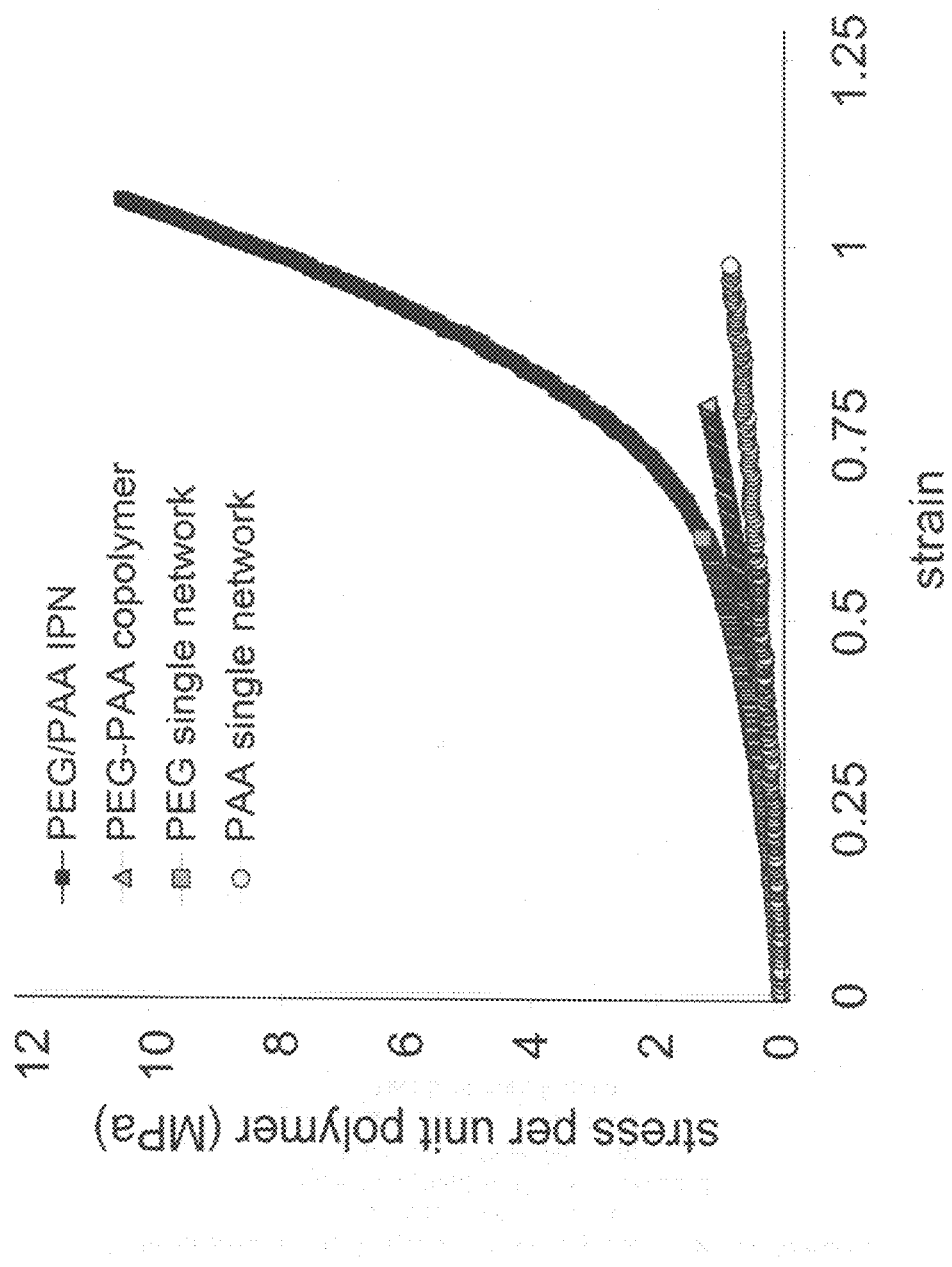
FIG. 3 shows the tensile strength of a representative interpenetrating polymer network hydrogel according to the present invention.

Our extensometry studies show that IPN hydrogels possess a number of important mechanical properties that make them excellent candidates for corneal prostheses. We have tested IPN hydrogels composed of PEG-DA (50% w/v in $dH_2O$) in the preparation state of the first network and polyacrylic acid (50% v/v in $dH_2O$) in the preparation state of the second network. The telechelic macromonomer PEG-DA will be referred to as simply PEG hereafter for brevity. We compared the strength of these IPN hydrogels to single networks of PEG or PAA, as well as copolymers of PEG and PAA. The samples were tested on an Instron Materials Tester and normalized for thickness as well as polymer content (based on the weight fraction of polymer in the hydrogel). The calculated true stress per unit solid (megapascals) and strain (fraction of original length) data are shown in FIG. 3. FIG. 3 shows that PEG/PAA IPNs are much stronger than either the individual polymer networks or copolymers. The effect of IPN formation on tensile strength is non-linear, as the maximum strength is many times higher than that of a PEG-PAA copolymer.

Figure 4:
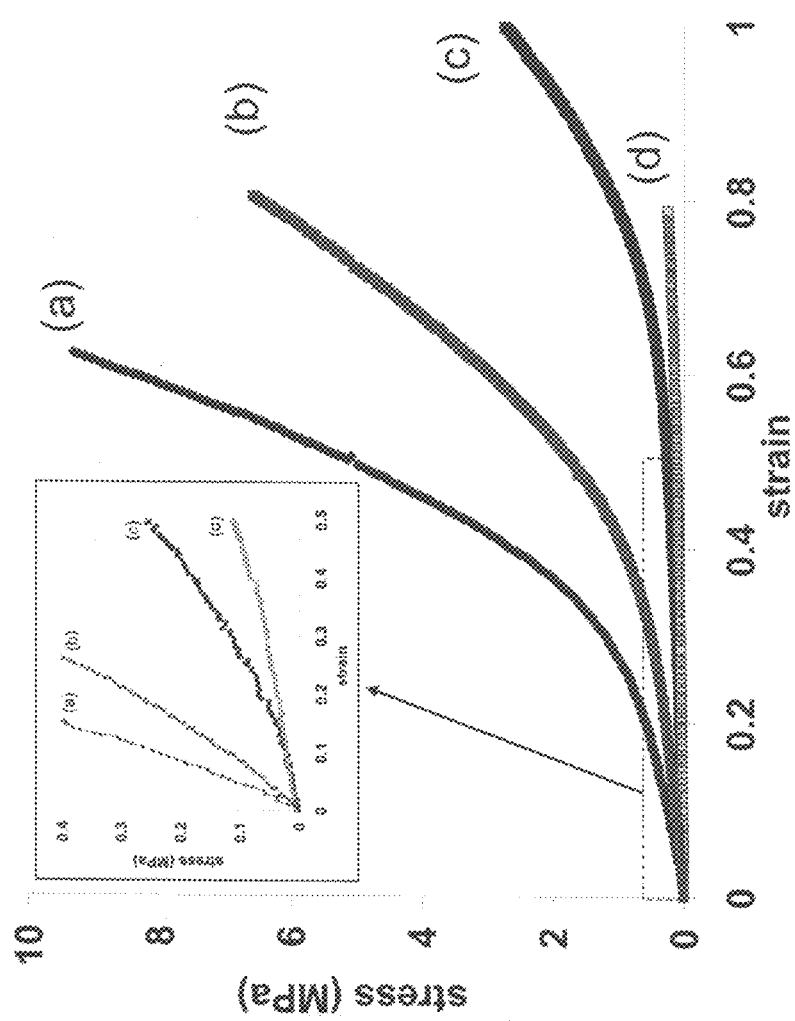
FIG. 4 shows relationship between tensile strength and PEG molecular weight for interpenetrating polymer network hydrogels according to the present invention.

The elastic moduli and tensile strength of the IPNs can be modified by changing the molecular weight of the PEG macromonomer used. For example, a range of PEG/PAA IPNs with PEG molecular weights from 575 Da to 20,000 Da have been synthesized. It was found that optically clear hydrogels may be formed from any of this range of molecular weights. However, as shown in FIG. 4, the tensile strength of the hydrogel varies depending on the MW of PEG used. FIG. 4 shows results obtained using (a) PEG(3400), (b) PEG(4600), (c) PEG(8000) and (d) PEG(14000). FIG. 4 shows that use of lower molecular weight PEG results in stronger hydrogels.

Figure 5:
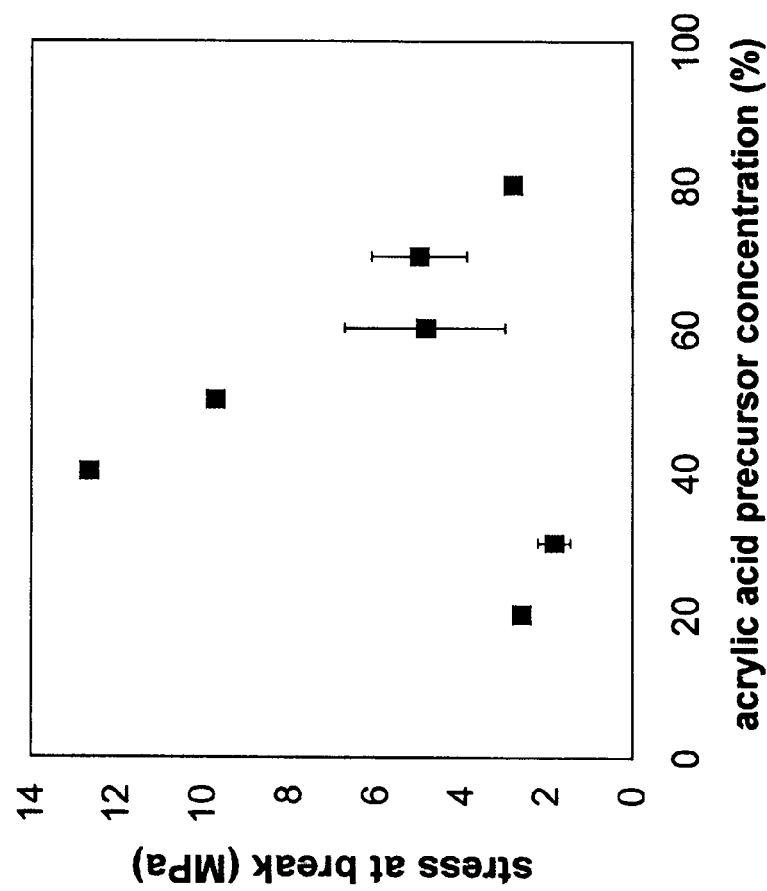
FIG. 5 shows relationship between stress-at-break and acrylic acid precursor concentration for interpenetrating polymer network hydrogels according to the present invention.
Figure 6:
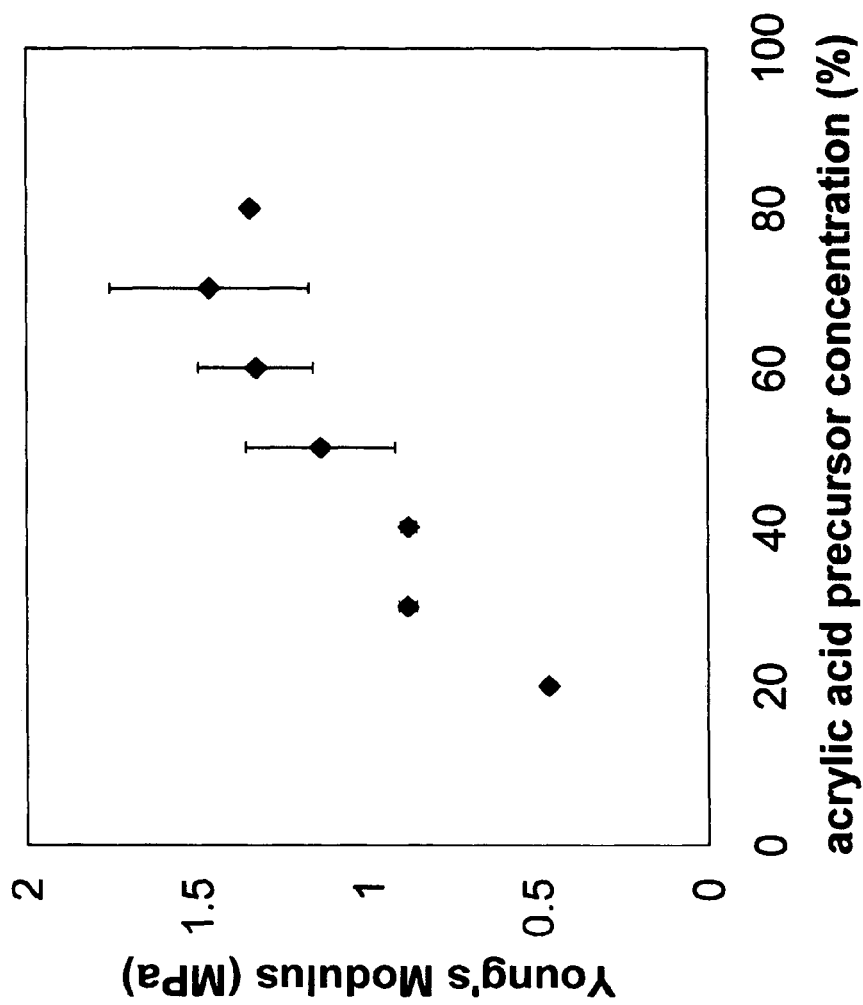
FIG. 6 shows relationship between Young's modulus and acrylic acid precursor concentration for interpenetrating polymer network hydrogels according to the present invention.

The elastic moduli and tensile strength of the IPNs can also be modified by changing the amount of acrylic acid used in the IPN. FIG. 5 shows stress-at-break values of PEG(4600)/PAA IPNs prepared from varying acrylic acid precursor solution concentrations in the preparation state of the second network. The strongest IPNs used 40% acrylic acid to prepare the second network. FIG. 6 shows Young's modulus values of PEG(4600)/PAA IPNs prepared from varying acrylic acid precursor solution concentrations in the preparation state of the second network. In general, the Young's modulus increases with increasing concentrations of acrylic acid in preparation of the second network.

Materials according to the present invention, as well as corneal prostheses made from these materials, preferably have a tensile strength on the order of 1 MPa, more preferably at least 1 MPa, most preferably between about 1 and 5 MPa.

Oxygen Permeability

IPN hydrogels composed of a PEG first network with MW 8000 and concentration of 50% w/v in dH₂O in the preparation state, and a second network of polyacrylic acid with 50% v/v in dH₂O in the preparation state were used to test oxygen permeability. The hydrogels were first rinsed in distilled water, then soaked in phosphate buffer solution for at least 24 hrs. The harmonic thickness of the hydrogel was then measured using Electronic thickness gauge Model ET-3 (Rehder Development company). The hydrogel was then soaked again in phosphate buffered saline solution for at least 24 hrs. Next, an electrode assembly (Rehder Development company) was attached to a polarographic cell and electrical cables were attached between the electrode assembly and a potentiostat (Gamry instruments). About 1.5 L of buffer solution was then saturated with air for at least 15 minutes and preheated to 35° C. Next, the hydrogel was carefully placed onto the electrode, the gel holder was placed over the hydrogel, and a few drops of buffer solution were placed on top of the hydrogel to keep the hydrogel saturated with buffer solution. The central part of the cell was then attached onto the cell bottom and the top part of the cell, containing the stirring rod, impeller, and coupling bushing, was attached to the top part of the cell. Air saturated buffer solution at 35° C. was then poured into the assembled cell and filled almost to the top. Next, heating coiled tubing was placed around the cell, the tubing was connected to the heating bath, insulation was wrapped around and on top of the cell, and the flow of heating fluid was turned on. The speed was then set at 400 rpm and current data was collected until the steady state was reached. The speed was then reset in 100 rpm increments up to 1200 rpm, and data was again collected. This data was then used to get the oxygen permeability by plotting the inverse of steady current versus the Reynolds number to the minus ⅔. An oxygen permeability of 95.9±28.5 Barrers was obtained. Materials according to the present invention, as well as corneal prostheses made from these materials, preferably have an oxygen permeability of more than about 15 Barrers, more preferably at least about 60 Barrers, most preferably at least about 90 Barrers.

Equilibrium Water Content

The water content of the hydrogels was evaluated in terms of the swollen-weight-to-dry-weight ratio. The dry hydrogel was weighed and then immersed in water as well as phosphate buffered saline. At regular intervals, the swollen gels were lifted, patted dry, and weighed until equilibrium was attained. The percentage of equilibrium water content (WC) was calculated from the swollen and dry weights of the hydrogel:

$$WC = \frac{W_s - W_d}{W_s} \times 100$$

where $W_s$ and $W_d$ are the weights of swollen and dry hydrogel, respectively.

Figure 7:
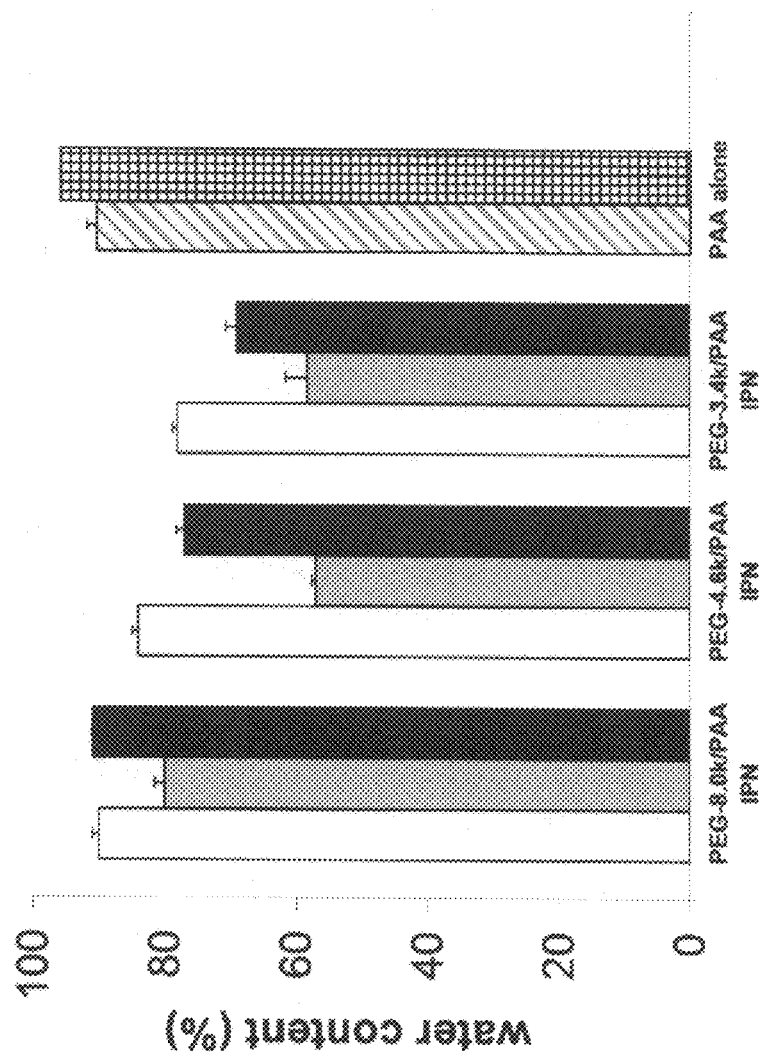
FIG. 7 shows representative equilibrium water contents for hydrogels according to the present invention.

The parameters varied to obtain hydrogels with differing water content were the molecular weight of the PEG macronomomer, the weight fraction of PAA in the second network, as well as the amount of crosslinking agent (e.g. triethylene glycol dimethacrylate, or low molecular weight PEG-DA) added to the first or second networks. FIG. 7 shows equilibrium water content data for PEG networks of varying macromonomer MW (white bars), and PEG/PAA IPNs made with PEG macromonomers of varying MW in deionized water (gray bars) and in the ionizing conditions of PBS, pH 7.4 (black bars). The water content data for the PAA network alone in deionized water (gray diagonal-patterned bars) and in PBS, pH 7.4 (black square-patterned bars) is shown on the right as a basis for comparison.

Table 1 shows the effect of varying the concentration of acrylic acid monomer used to prepare the second network on the equilibrium water content of PEG/PAA IPNs. In general, lower concentrations of acrylic acid monomer leads to hydrogels with higher equilibrium water content.

TABLE 1

Equilibrium Water Content of PEG(8.0k)/PAA hydrogels with varying preparation concentration of acrylic acid (AA) monomer

| Concentration of AA in the preparation state | Equilibrium Water Content of PEG/PAA IPN |
| --- | --- |
| 30% | 99% |
| 40% | 91% |
| 50% | 83% |

Materials according to the present invention, as well as corneal prostheses made from these materials, preferably have an equilibrium water content of between about 20-95%, more preferably between about 70-90% or between about 20-60%.

Because different MWs of PEG and different starting concentrations of acrylic acid result in different amounts of equilibrium water content, the final amount of PEG and PAA in the hydrogel varies depending on the MW of the starting PEG used and the concentration of acrylic acid used. Examples of compositions of varying weight ratios of PEG and PAA that have been made according to the present invention are shown in Table 2. The compositions in this table were all made using a starting concentration of 50% PEG macromonomers.

TABLE 2

Compositions of PEG(8.0k)/PAA IPNs with varying preparation concentration of AA monomer

| Concentration of AA in the preparation state | Dry Wt. % PEG in IPN | Dry Wt. % PAA in IPN | (Dry Wt.PEG)/ (Dry Wt. PAA) |
| --- | --- | --- | --- |
| 30% | 23.5% | 76.5% | 0.30 |
| 40% | 17.5% | 82.5% | 0.20 |
| 50% | 13.0% | 87.0% | 0.15 |

Optical Clarity

The percentage (%) of light transmittance of IPN hydrogels composed of PEG (50% w/v in dH₂O) in the preparation state of the first network and polyacrylic acid (50% v/v in dH₂O) at 550 nm was also measured using a Varian Cary 1E/Cary 3E UV-Vis spectrophotometer following the method described by Saito et al (Saito et al, "Preparation and Properties of Transparent Cellulose Hydrogels", Journal of Applied Polymer Science, Vol. 90, 3020-3025 (2003)). The refractive index of the PEG/PAA hydrogel (with PEG MW 8000) was measured using an Abbe Refractometer (Geneq, Inc., Montreal, Quebec). The percentage of light transmittance was found to be 90%, and the refractive index was found to be 1.35. Materials according to the present invention, as well as corneal prostheses made from these materials, are preferably at least about 70% transparent.

Nutrient Permeability

We studied the glucose permeability across PEG/PAA IPNs, PEG polymers of varying molecular weight, PAA polymers, and PHEMA polymers, as well as human, bovine, and pig corneas in vivo using a modified blind well chamber apparatus developed in our laboratory. In these experiments, non-porous mylar and dialysis membranes (MWCO 12 kD-14 kD) were used as negative and positive controls, respectively. Glucose diffusion coefficients for PEG/PAA (1.10 mm thick) and PHEMA hydrogels (0.250 mm thick) were calculated using Fick's law and taking into account the sample thicknesses. Similarly, glucose diffusion coefficients for human, bovine, and pig corneas were also calculated taking into account corneal thicknesses. Our results indicate that PEG/PAA IPNs ($D_{PEG-DA/PAA}=9.0\pm1.2\times10^{-07}$ cm$^2$/s) are more permeable than PHEMA ($D_{PHEMA}=2.7\pm0.7\times10^{-08}$ cm$^2$/s), with a p value of <0.05. This is consistent with the published values of the diffusion coefficient of pHEMA membranes ($D_{PHEMA}\sim10^{-08}$ cm$^2$/sec), which is about two orders of magnitude less than that of the human, bovine, rabbit and pig corneas we have measured in vitro, which are all on the order of $D\sim10^{-06}$ cm$^2$/sec)). This difference is largely due to the lower water content of PHEMA (40%), for the hydration of a material is known to be an important indicator of its permeability. The results from this study indicate that the PEG-DA/PAA IPN is able to facilitate adequate passage of glucose to an overlying epithelial cell layer.

Figure 8:
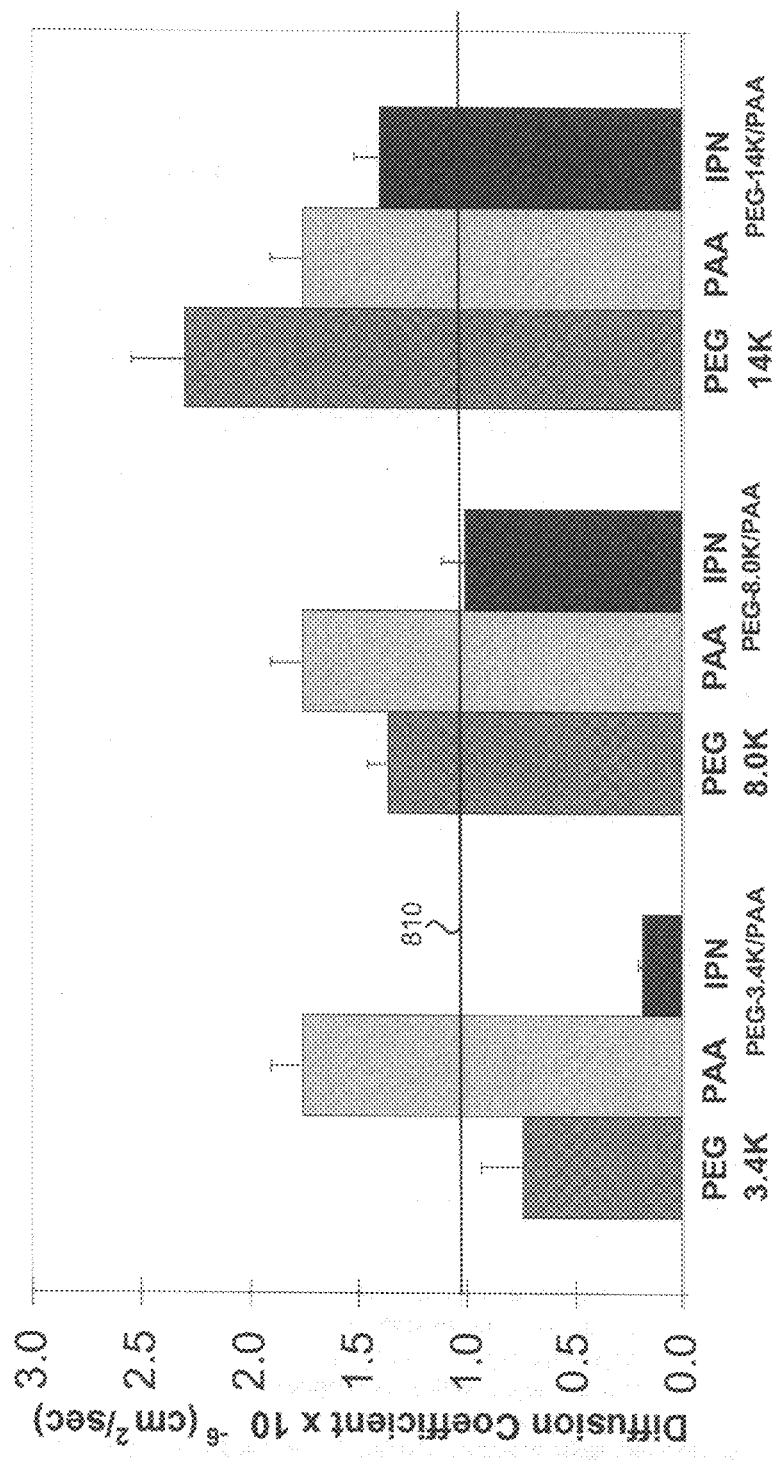
FIG. 8 shows relationship between PEG molecular weight and glucose concentration for interpenetrating polymer network hydrogels according to the present invention.

We next compared PEG/PAA IPNs made with different MW PEG to single networks made of PEG or PAA. The results are shown in FIG. 8, with line 810 indicating the diffusion constant of human cornea. The results show that glucose permeability changes depending on the MW of PEG in the network. The threshold of permeability should be between $10^{-05}$-$10^{-07}$ cm$^2$/sec, which is the physiologic range necessary to sustain healthy corneal tissue.

Surface Modification of IPN Hydrogels

Materials according to the present invention have biomolecules covalently linked to the IPN hydrogels. These biomolecules may, e.g., promote epithelial cell adhesion and proliferation on the nonadhesive hydrogel surface. The biomolecules are preferably proteins, polypeptides, amino acids, carbohydrates, or nucleic acids. More preferably, the biomolecules are at least one of cell adhesion molecules, immunoglobulins, or growth factors. Most preferably, the biomolecules are biomolecules found in the cornea and/or aqueous humor (e.g. collagen type I) or derivatives thereof.

Biomolecule linkage could be accomplished using two approaches: (1) incorporation of biomolecules directly into the IPN during its synthesis and (2) subsequent attachment of biomolecules to synthesized hydrogels. The latter approach may rely, e.g., on (a) photoinitiated attachment of azidobenzamido peptides, (b) photoinitiated functionalization of hydrogels with an N-hydroxysuccinimide group followed by reaction with peptides/proteins, or (c) chemoselective reaction of aminooxy peptides with carbonyl-containing polymers.

To incorporate peptides directly into IPN hydrogels, the peptides can be reacted with acryloyl-PEG-NHS to form acrylate-PEG-peptide monomers. (See Mann et al. (2001) in a paper entitled "*Smooth muscle cell growth in photopolymerized hydrogels with cell adhesive and proteolytically degradable domains: synthetic ECM analogs for tissue engineering*" and published in "*Biomaterials* 22:3045-3051"; Houseman et al. (2001) in a paper entitled "*The microenvironment of immobilized Arg-Gly-Asp peptides is an important determinant of cell adhesion*" and published in "*Biomaterials* 22(9):943-955"; and Hern et al. (1998) in a paper entitled "*Incorporation of adhesion peptides into nonadhesive hydrogels useful for tissue resurfacing*" and published in "*J. Biomed. Mater. Res.* 39(2):266-276"). These peptide-containing acrylate monomers can be copolymerized with other desired acrylates, including PEG-diacrylates, using standard photopolymerization conditions to form peptide-containing hydrogels. The major advantage of this approach is that the peptide is incorporated directly into the hydrogel, and no subsequent chemistry is needed.

For example, an RGD peptide could be used to form an acrylate-PEG-RGD monomer. This monomer could be copolymerized with PEG-DA in forming the first polymer network or with other acrylates in forming the second polymer network. Peptide incorporation could be confirmed by structural characterization of the hydrogels using attenuated total reflectance/Fourier transform infrared (ATR/FTIR) spectroscopy and X-ray photoelectron spectroscopy (XPS). Additional peptides could be used to make new monomers and corresponding hydrogels.

Alternatively, biomolecules may be attached to polymerized hydrogels. In this approach, proteins/peptides are attached with the polymers using (a) photoinitiated reaction of azidobenzamido biomolecules (e.g. proteins and/or polypeptides) or (b) photoinitiated functionalization of hydrogels with an N-hydroxysuccinimide group followed by reaction with biomolecules such as peptides and proteins. This method can be used to attach one type of biomolecule or a combination of different biomolecules to the surface of hydrogels.

Figure 9:
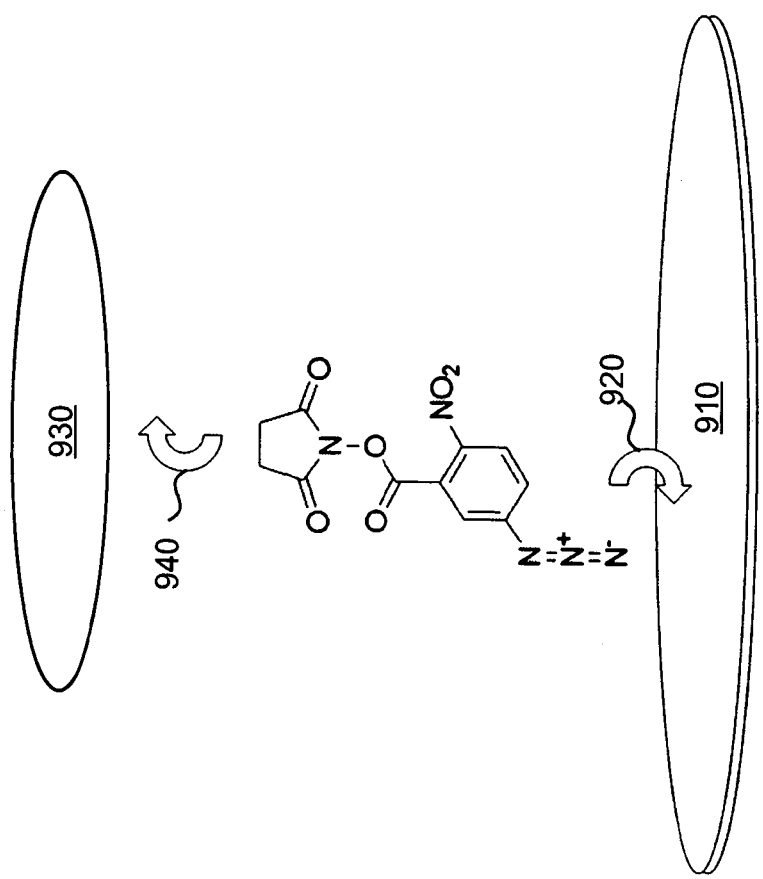
FIG. 9 shows a schematic of biomolecule linkage according to the present invention.

Azidobenzamido groups react with light (250-320 nm, 5 min) to generate aromatic nitrenes, which insert into a variety of covalent bonds. In a preferred embodiment, biomolecules such as proteins and/or peptides are fixed to the artificial cornea photochemically. For the photochemical fixation of peptides/proteins to the hydrogel surfaces, an azide-active-ester chemical containing a photoreactive azide group on one end and an NHS end group (which can conjugate cell adhesion proteins and peptides) on the other end is used. With this method, shown schematically in FIG. 9, a solution of 5-azido-2-nitrobenzoic acid N-hydroxysuccinimide ester is spread over the hydrogel surface 910. This can be accomplished by dissolving 5 mg of 5-azido-2-nitrobenzoic acid N-hydroxysuccinimide ester in 1 mL of N,N-dimethylformamide (DMF) (See Matsuda et al. (1990) in a paper entitled "*Development of micropatterning technology for cultured cells*" and published in "*ASAIO Transactions* 36(3):M559-562") and spreading the solution over hydrogel surfaces. After air drying the hydrogel, it is then exposed to UV irradiation 920, for example for 5 minutes. Upon UV irradiation, the phenyl azide group reacts to form covalent bonds with the hydrogel surface 910. The irradiated surfaces are then thoroughly rinsed with solvent to remove any unreacted chemicals from the surface. The hydrogels are then incubated for 24 hours in a solution containing the amine-containing biomolecule of interest 930 (e.g. collagen type I), which reacts 940 with the exposed NHS end groups. For the purpose of the present invention, biomolecules present in the cornea and/or aqueous humor, or derivatives thereof, would be candidates for attachment to hydrogels.

Both analytical and chemical approaches can be used to validate the present methods. Peptide attachment can be confirmed by structural characterization of the hydrogels using ATR/FTIR spectroscopy, XPS and at times amino acid and elemental analysis of the polymers. The attachment strategies can also be validated by using peptides labeled with fluorescent or visible dyes and by use of dynamic contact angle measurements.

Figure 10:
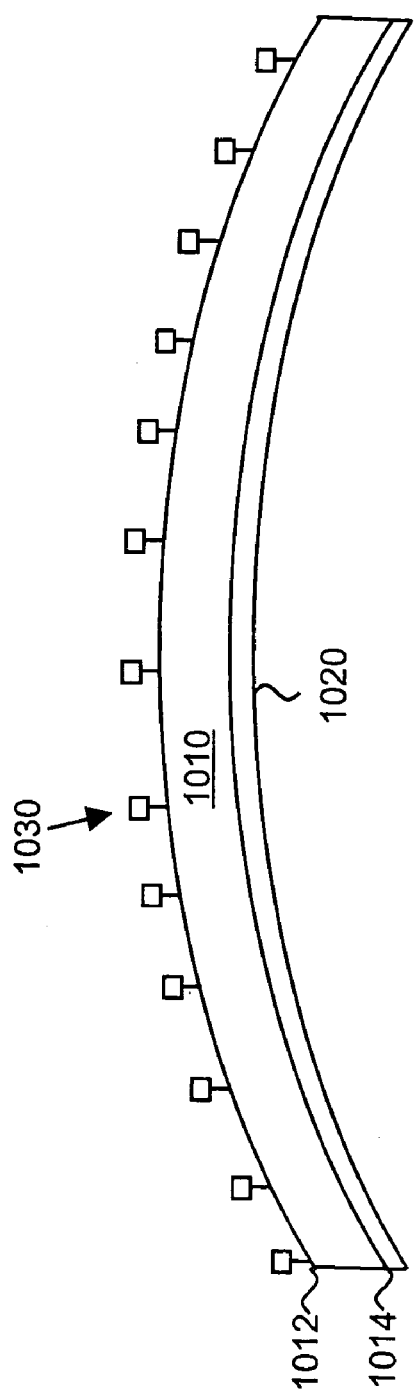
FIG. 10 shows surface modification of a material according to the present invention.

In addition to, or as an alternative to proteins, polypeptides, or amino acids, the IPN hydrogel may be modified with carbohydrates or other macromonomers. In one aspect of this embodiment, one or both surfaces is modified with a layer of PEG macromonomers, polymerized PEG macromonomers, polymerized PEG-DA, polymerized PEG-DMA, polymerized PEG-acrylate or polymerized PEG-methacrylate, to reduce protein absorption of the material. The layer may be bulk polymerized on the surface of the hydrogel either as an interpenetrating network or as a network covalently anchored to the surface. Alternatively, PEG chains can be covalently tethered to the surface of the hydrogel by utilizing 5-azido-2-nitrobenzoic acid N-hydroxysuccinimide ester and an amine-terminated PEG macromonomer. This method can also be adapted to attach biomolecules with PEG macromonomer spacer arms between the biomolecule and the hydrogel surface. FIG. 10 shows a corneal prosthesis 1010 with surfaces 1012 and 1014. In this example, surface 1014 is modified with PEG macromonomer layer 1020, and surface 1012 is modified with proteins 1030, although both or neither surface may be modified.

Corneal Prosthesis

In one embodiment of the present invention, the inventive material is used as a corneal prosthesis. The corneal prosthesis may be, e.g., an artificial cornea, corneal onlay, corneal inlay, or corneal implant. In a preferred embodiment, the material is used as an artificial cornea.

Figure 11:
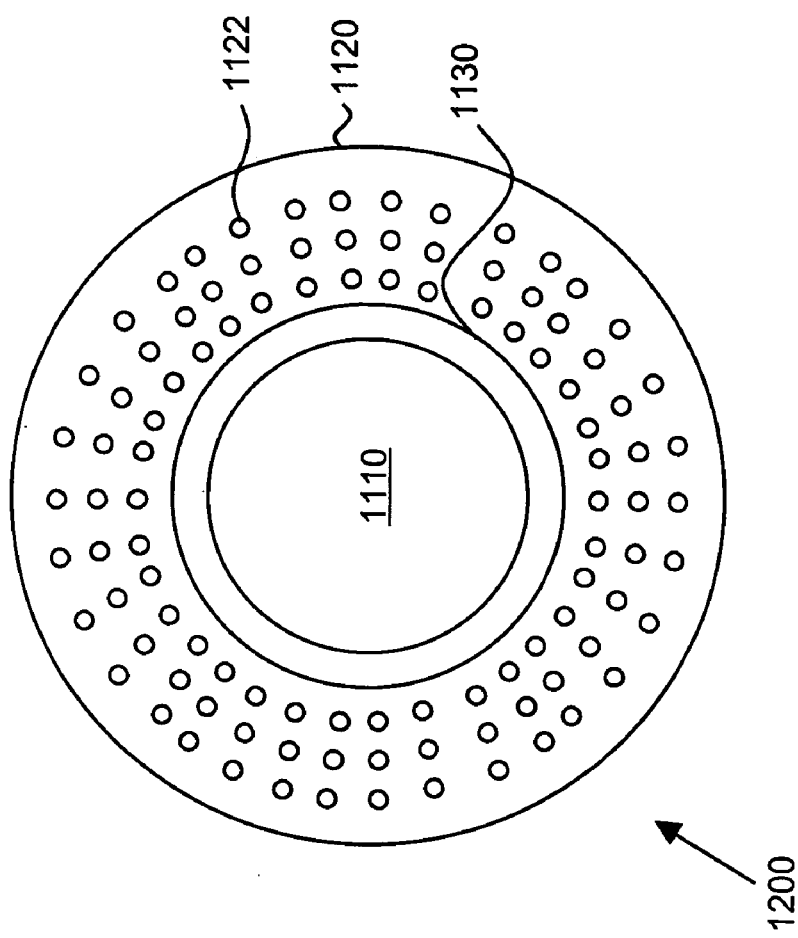
FIG. 11 shows a schematic of an artificial cornea according to the present invention.

FIG. 11 is a schematic of an artificial cornea 1100 according to one embodiment of the present invention. Artificial cornea 1100 contains an optically clear central core 1110, made of the IPN hydrogel material described above, and a hydrophilic, hydrogel-based, biocompatible skirt 1120. Skirt 1120 contains pores 1122 to enable integration with stromal tissue and diffusion of nutrients through artificial cornea 1100. Optionally, artificial cornea 1100 may also contain an interdiffusion zone 1130, in which central core 1110 interpenetrates skirt 1120 or vice versa. Exemplary dimensions of artificial cornea 1100 are as follows: 4.0-12.0 mm total diameter, 3.5-10.0 mm central core diameter, and 15-2000 µm central core and skirt thickness. Pores 1122 preferably have a diameter of between about 20 µm and about 200 µm.

Artificial cornea 1100 preferably has a nutrient diffusion coefficient sufficient to allow passage of nutrients through the artificial cornea. Preferably, central core 1110 has a nutrient diffusion coefficient in the range of about $10^{-5}$ cm$^2$/sec to about $10^{-7}$ cm$^2$/sec. Nutrients diffusible through the artificial cornea may be, for example, glucose, growth factors, etc. The diffusion coefficient can be controlled by changing the relative mesh size of the first and second networks, which can in turn be accomplished by changing the molecular weight of the telechelic macromonomer used in the IPN (see above).

The skirt of the artificial cornea may be made of an IPN hydrogel, as described above, or a single network hydrogel. In one embodiment, both the core and skirt is made of PEG/PAA of the same or different relative composition (by dry weight and molecular weight) of PEG and PAA. In another embodiment, the skirt is made of PHEA, which is a hydrophilic, biocompatible, and rapidly photopolymerizing network that can be patterned with high fidelity. In addition, PHEA can interpenetrate into another network prior to polymerization to form a "seamless" core-skirt junction. With any skirt material, the central core and skirt of the artificial cornea may be joined together through an interdiffusion zone, in which the central core component interpenetrates the skirt component or vice versa.

Preferably, biomolecules are attached to the material in a site-specific manner, e.g. using photolithography. In a particularly preferred embodiment, the bulk and posterior of a corneal prosthesis' central core will remain unmodified to maintain the intrinsic passivity to protein adsorption of the hydrogel and enable long-term optical clarity. Alternatively, the central core may be modified with PEG, as described above. Additionally, pores in the skirt may be selectively tethered with biomolecules that mimic the extracellular matrix of the corneal stroma to encourage tissue integration while minimizing scar formation.

Figure 12:
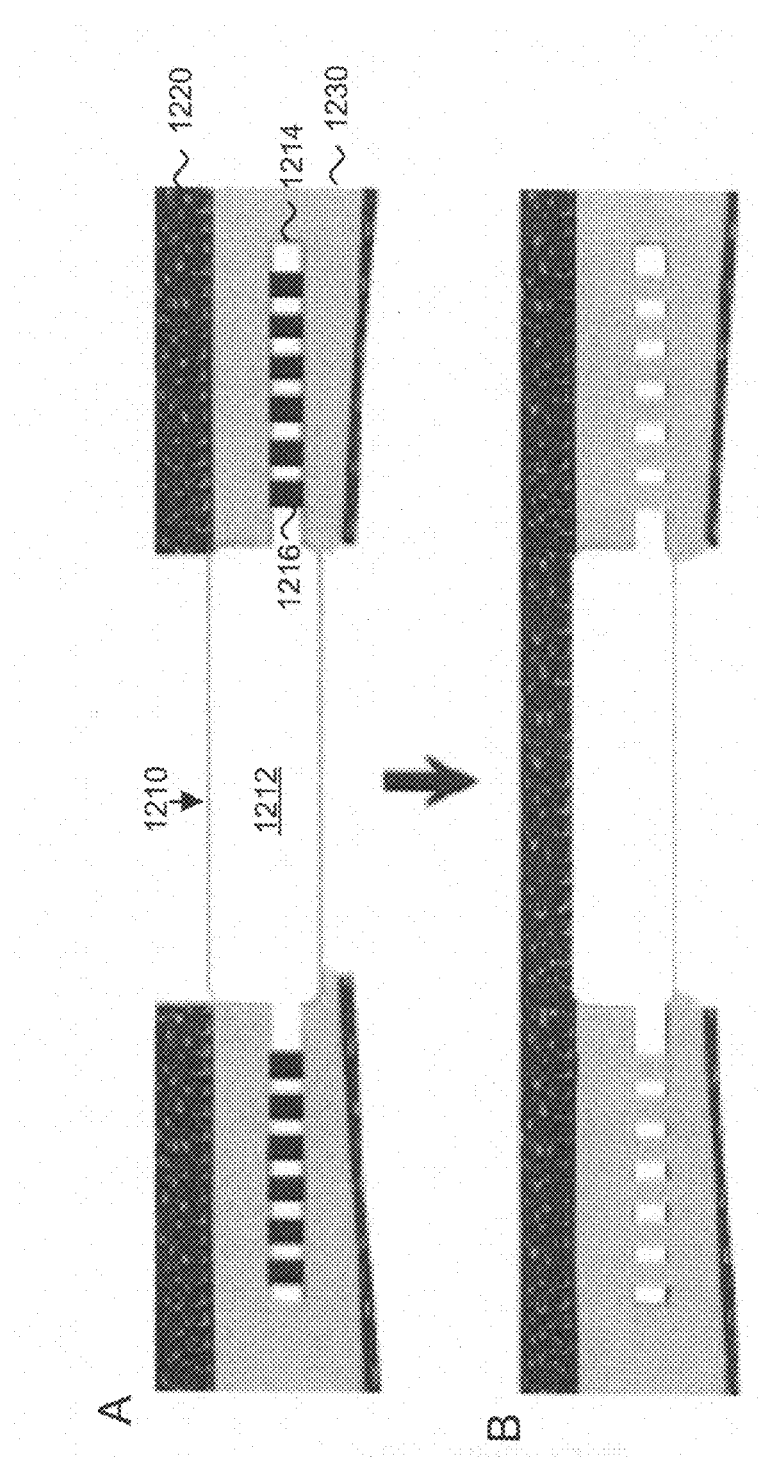
FIG. 12 shows a schematic of tissue integration of an artificial cornea according to the present invention.

FIG. 12 shows a schematic of how a biomolecularly modified artificial cornea implant would function according to the present invention. Initially, epithelia 1220 would be removed and implant 1210, with core 1212 and skirt 1214, with pores 1216, will be implanted into stroma 1230 (FIG. 5A). In time, epithelial layer 1220 will grow over the core 1212 and the stroma will grow through the pores 1216 to give a fully tissue integrated implant 1210 (FIG. 12B). The implant may also have epithelial cells, or other cornea derived cells, already attached to the implant prior to implantation.

Figure 13:
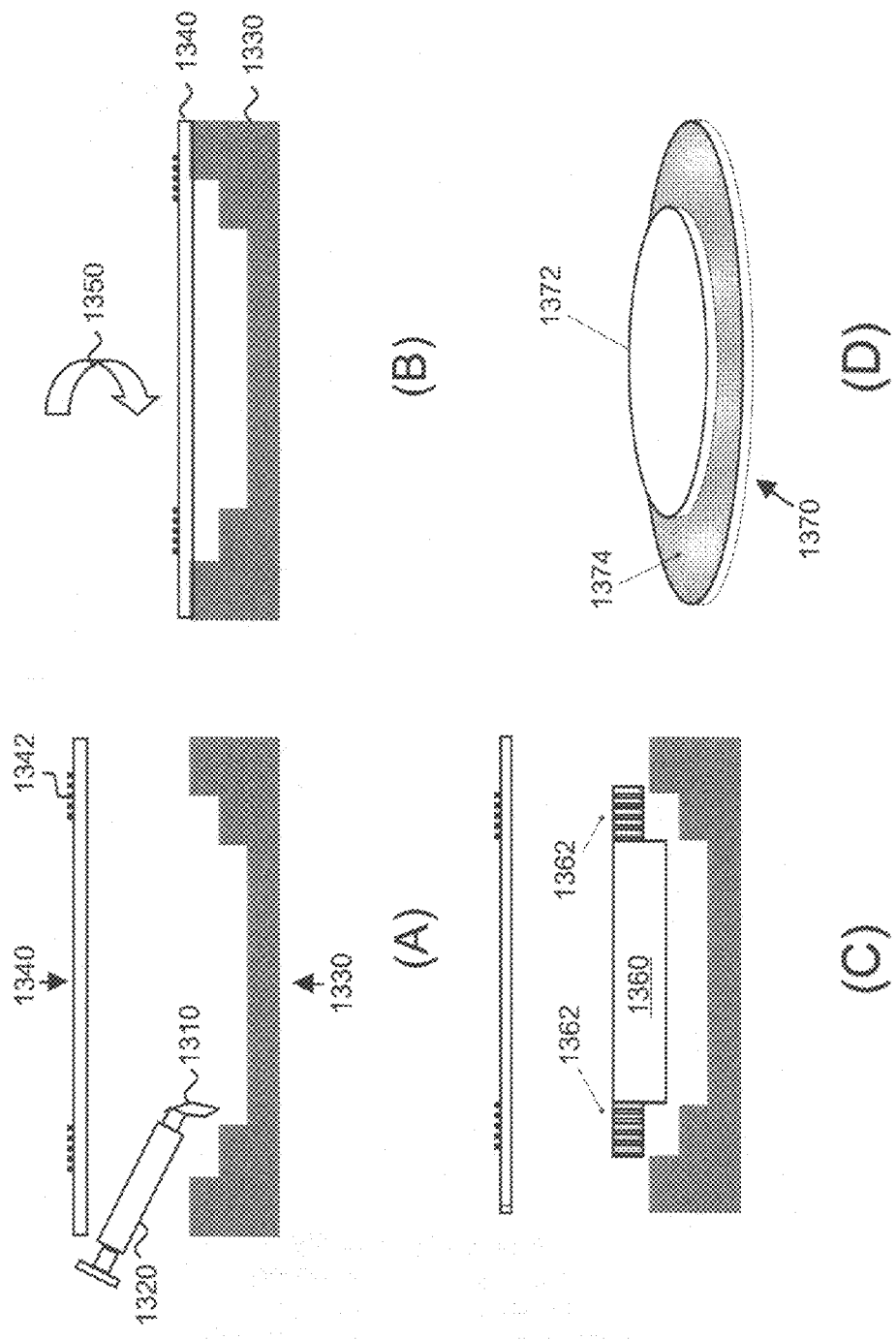
FIG. 13 shows a schematic of a method of fabricating an artificial cornea according to the present invention.

An exemplary protocol for synthesizing an artificial cornea according to the present invention is shown in FIG. 13. Hydrogel precursors 1310 are injected with syringe 1320 into a two-level Teflon mold 1330 and then covered with a photomask 1340 with UV blocking discs 1342 (FIG. 13A). Either the same or different precursors can be used in the different levels. The levels may be the same or different thickness, and may be any shape, e.g., curved. UV light 1350 is then passed through the mask, completely polymerizing the contents of the mold except for the regions in the periphery below UV-blocking discs 1342 (FIG. 13B). When removed from the mold, the polymerized hydrogel 1360 is left with a pattern of micrometer-sized channels 1362 in its periphery (FIG. 13C). An IPN hydrogel can then be formed by swelling the entire construct in a second monomer solution, dabbing the excess monomer off, and then exposing the entire swollen hydrogel to UV light. The final result is a construct 1370 with a transparent center optic 1372 and a porous periphery 1374 (FIG. 13C). This construct can then be coated with biomolecules, e.g. by azide-active-ester linkage, on its anterior surface as well as in the peripheral skirt region, as described above. The artificial cornea would then be washed thoroughly (e.g. for 1 week in dH$_2$O) to wash away unreacted monomers before integrating.

In an alternative procedure, the IPN hydrogel core of desired dimensions is synthesized first, washed, and then positioned within a mold under the photomask for the skirt. The skirt monomer (e.g. hydroxyethyl acrylate), photoinitiator and crosslinker, are then injected around the periphery of the core and allowed to interdiffuse into it for a designated period of time (30 seconds to 1 hour). The solution is then exposed to UV light through the photomask to polymerize the skirt around the core; the two are thus connected by the skirt polymer, which has diffused into the periphery of the core polymer. An IPN hydrogel skirt can be created by the methods already described, except that after removing excess monomer, only the peripheral region is exposed to UV light to ensure that polymerization is localized to the skirt. (This ensures that a third network is not created in the core region, but a second network is created in the skirt region).

Figure 14:
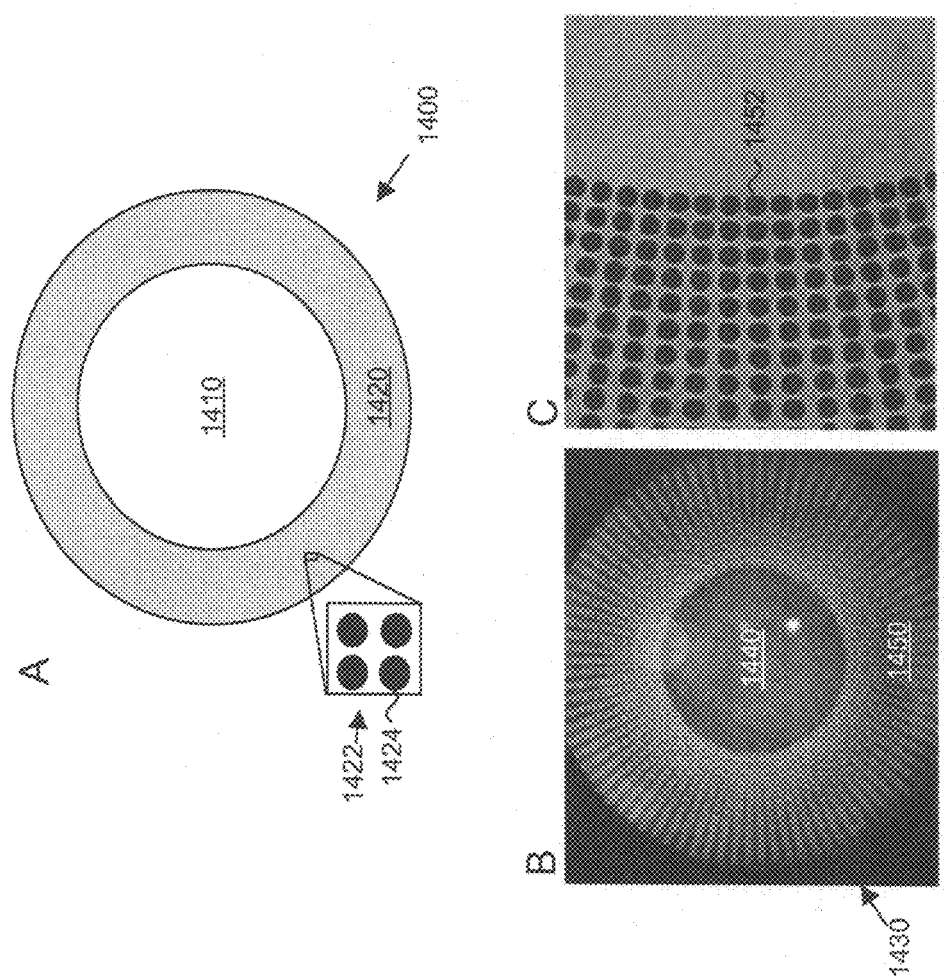
FIG. 14 shows a schematic (A) and an actual (B, C) photomask useful for fabricating an artificial cornea according to the present invention.
Figure 15:
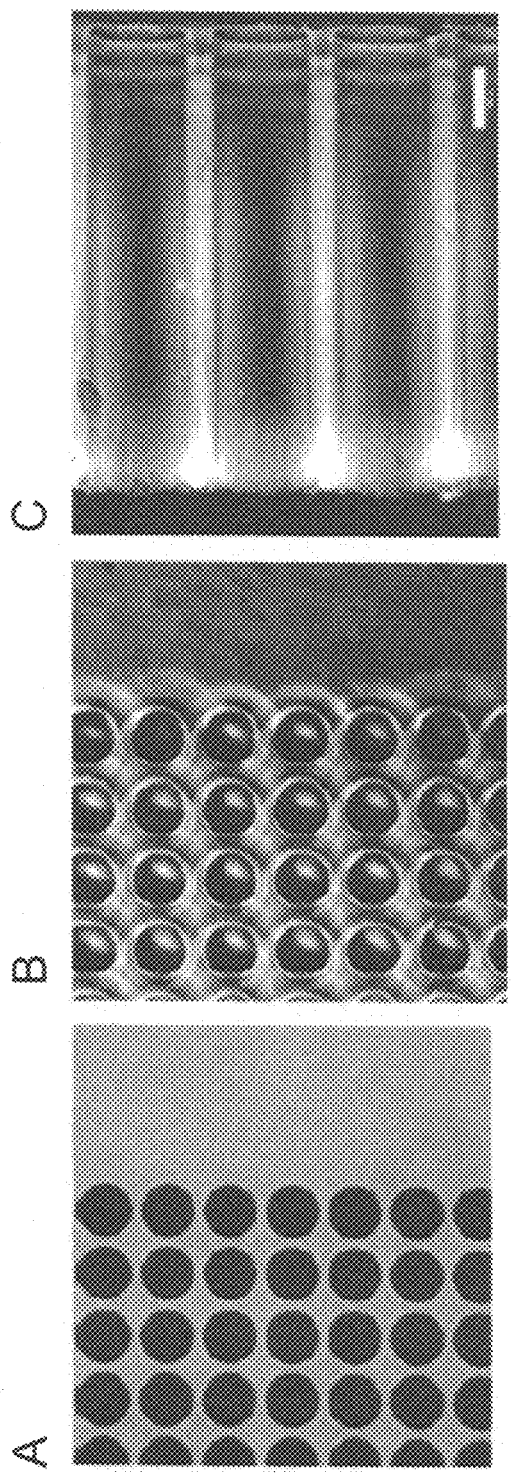
FIG. 15 shows an example of a photomask (A) and the resulting hydrogel (B, C) formed using a photomask according to the present invention.

FIG. 14 shows a schematic (A) and an actual (B, C) photolithographic mask that may be used to synthesize porous hydrogel skirts. Mask 1400 contains an unmasked central region 1410, for forming the central core, and a patterned, masked peripheral region 1420, for forming the peripheral skirt. Patterned peripheral region 1420 contains UV-blocking disks 1424, as shown in insert 1422. FIG. 14B shows an actual photolithographic mask 1430 that may be used according to the present invention. Discs may be made of any UV-blocking material, including but not limited to chrome, platinum, tungsten, copper, aluminum, gold, or ink, such as ink on a transparency using a high-resolution printer. This mask has a 2 cm unpatterned central region 1440, and a patterned peripheral region 1450 with 60 µm diameter discs 1452 spaced 10 µm apart along lines with 1° of separation. Discs 1452 can be clearly seen in the magnified view of mask 1430, shown in FIG. 14C. While the central region of this mask is 2 cm in diameter, other dimensions are possible. Similarly, other disc dimensions are possible, preferably ranging from about 20 μm to about 200 μm diameter. Any pattern of discs may be used, including but not limited to radial and grid patterns. For example, FIG. 15 shows a photomicrograph of a grid style chrome pattern (A), a representative resulting porous hydrogel after UV irradiation (B) and the porous hydrogel in cross section (C).

EXAMPLES

Photolithographically Patterned Artificial Cornea

Figure 16:
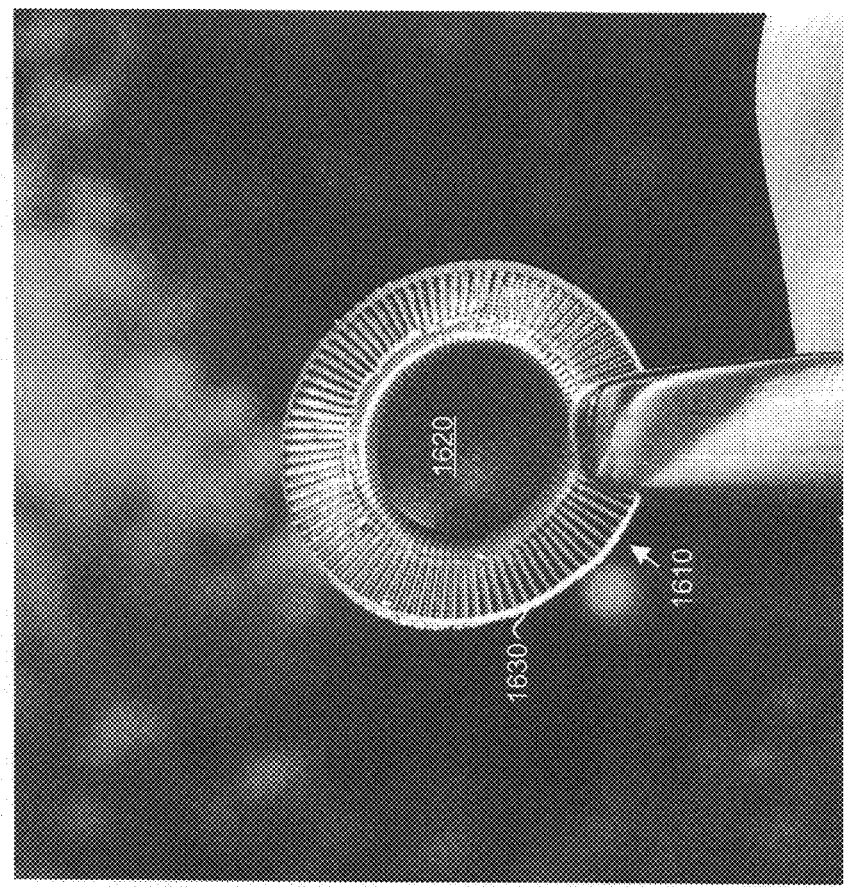
FIG. 16 shows a photomicrograph of an embodiment of an artificial cornea according to the present invention.

FIG. 16 shows a photomicrograph of a photolithographically patterned artificial cornea 1610 with optically clear central core 1620 and porous peripheral skirt 1630. In this example, the central core was made of a PEG/PAA IPN and the skirt was made of PHEA. The PEG/PAA IPN hydrogel was synthesized by a two-step sequential network formation technique based on UV initiated free radical polymerization. A precursor of the first solution was made of purified PEG-diacrylate (MW 8000) dissolved in deionized water with hydroxymethyl propiophenone as the UV sensitive free radical initiator. The solution was cast into a Teflon mold, covered with a glass plate, and reacted under a UV light source at room temperature. Upon exposure, the precursor solution underwent a free-radical induced gelation and became insoluble in water. To incorporate the second network, the PEG hydrogel was removed from the mold and immersed in a 50% v/v acrylic acid solution with 1% v/v hydroxymethyl propiophenone as the initiator, and 1% v/v triethylene glycol dimethacrylate as the cross-linking agent for 24 h at room temperature. The double network hydrogel was then washed extensively in Dulbecco's phosphate buffered saline and allowed to achieve equilibrium swelling. Next, a circular cutting tool was used to cut out a disc, which would become the central core component. The disc was then cast between a glass plate and the center of a photomask. A PHEA precursor solution was then injected around the central optic disc and the monomer was allowed to diffuse into the periphery of the optic for 15 minutes. The photomask was then placed under a UV light source for 60 seconds. The resulting core-skirt construct was then removed from the plates, washed extensively, and stored in phosphate buffered saline until further use.

Figure 17:
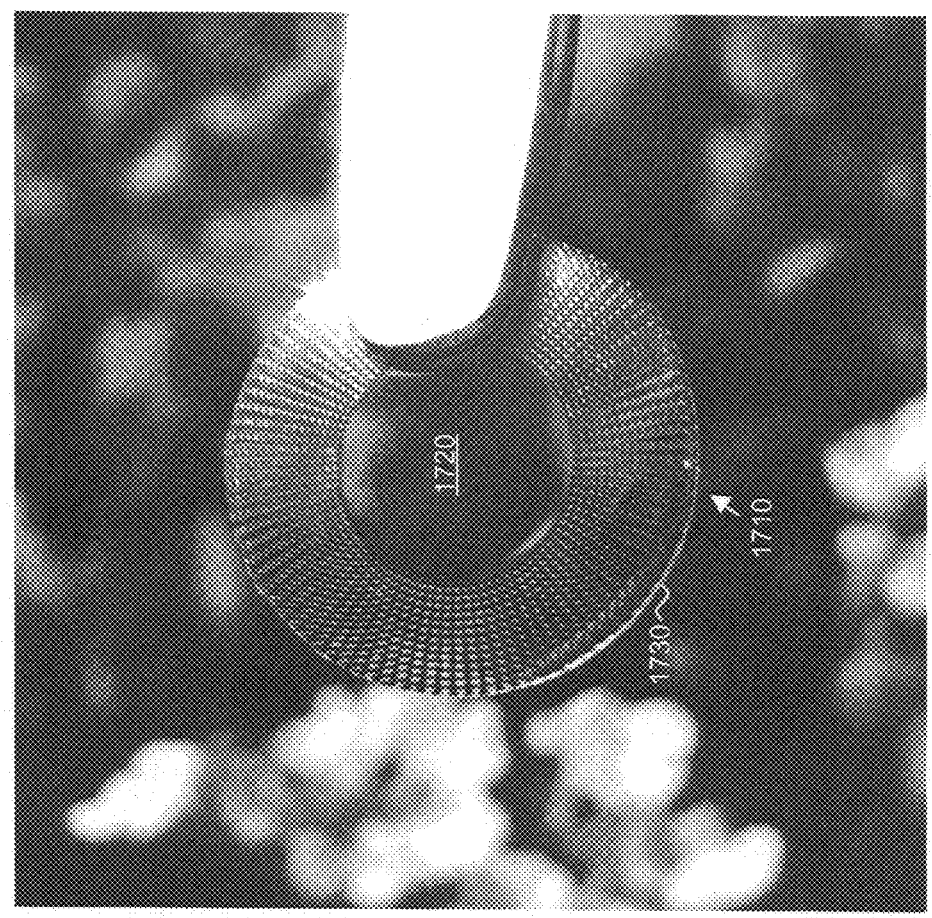
FIG. 17 shows a photomicrograph of another embodiment of an artificial cornea according to the present invention.

FIG. 17 shows a photomicrograph of a photolithographically patterned artificial cornea 1710 with optically clear central core 1720 and porous peripheral skirt 1730. In this example, both the central core and the skirt were made of a PEG/PAA IPN, and the artificial cornea was made as described in FIG. 13.

Site-Specific Biofunctionalization of with Collagen

Figure 18:
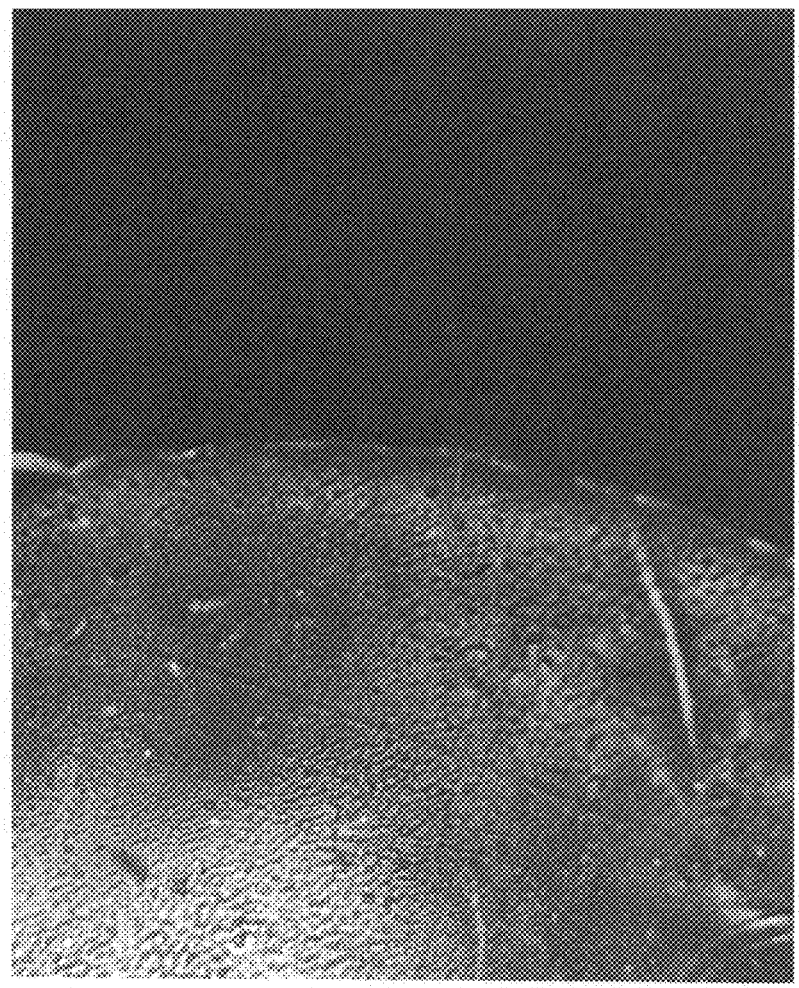
FIG. 18 shows an example of site-specific modification of a hydrogel with collagen according to the present invention.

PEG/PAA double network hydrogels were coated with the heterobifunctional photoreactive cross-linker 5-azido-2-nitrobenzoyloxy N-hydroxysuccinimide. The hydrogels were then exposed to a UV light source (75 W Xenon Lamp, Oriel Instruments) to induce covalent binding via the azide functional group. This leaves the N-hydroxysuccinimide group exposed for subsequent reaction with the primary amines of collagen type I. Hydrogels functionalized with azide-active-ester and unmodified hydrogels were incubated with 0.1% (w/v) collagen type I (Vitrogen); as a control, PEG/PAA was incubated in deionized water. Fluorescence microscopy was used to visualize the site-specific binding of isothiocyanate (FITC)-labeled collagen to the hydrogels, as shown in FIG. 18. The left side of FIG. 18 shows a gel surface reacted with Collagen-FITC and the right side shows an unreacted gel surface.

Growth of Cells on Hydrogels

Figure 19:
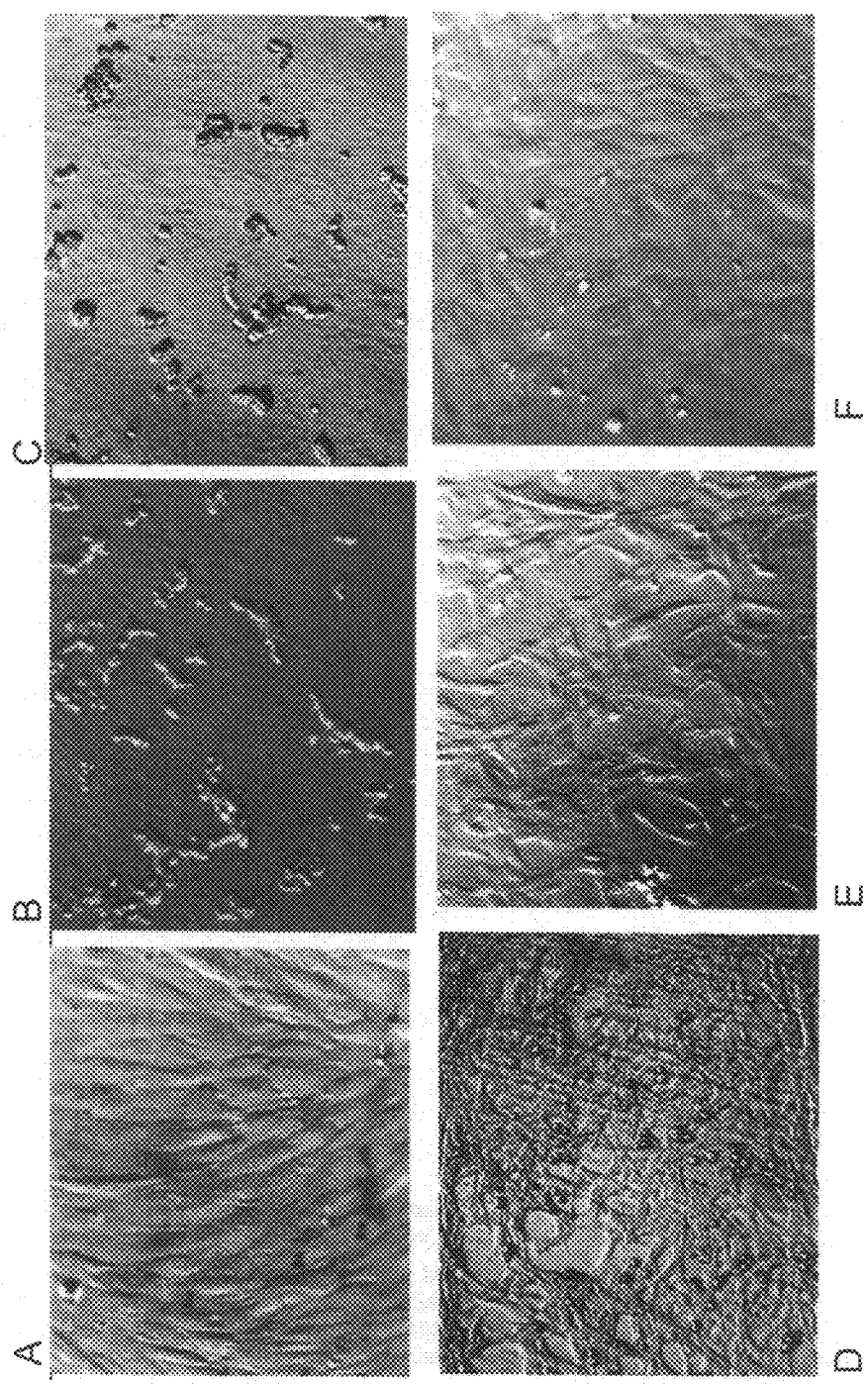
FIG. 19 shows examples of cellular growth on surface-modified hydrogels designed for corneal prosthesis applications according to the present invention.

Early passage rabbit corneal epithelial cells screened for epithelial differentiation were seeded on surface-modified PEG/PAA IPN hydrogels at a concentration of $1.0 \times 10^5$ cells/$cm^2$. The epithelial cells exhibited excellent spreading (>75%) on collagen-bound PEG/PAA IPNs within 2 hours, achieved confluency within 48 hours, and had migrated over the remainder of the unseeded surface by day 5. A representative photomicrograph of the adherent cells is shown in FIG. 19A. As expected, the unmodified double network did not promote cell attachment or spreading (not shown). In addition, cell spreading was not observed when hydrogels were incubated with collagen type I without prior azide-active-ester functionalization, indicating that little or no physical adsorption of proteins to PEG/PAA had taken place (FIG. 19B). FIG. 19C shows cells seeded on an unmodified hydrogel without any prior exposure to collagen or cell-adhesion promoting biomolecules. The lack of cell spreading indicates that the unmodified hydrogel does not support cellular adhesion. We have also attached other biomolecules as well as combinations of biomolecules to the hydrogel surface through azide-active-ester linkage. FIG. 19D shows corneal epithelial cells growing on a hydrogel surface tethered with RGD peptides, which was prepared in the following way. RGD peptides were reacted with 5-azido-2-nitrobenzoic acid N-hydroxysuccinimide ester in mixture of phosphate buffered saline and dimethyl formamide solution overnight, dropcasted onto the hydrogel surface, air-dried, and then exposed to UV light. The cells were seeded on the surface in the way described above, and the photomicrograph was taken after 24 hours. FIG. 19E shows corneal epithelial cells growing on hydrogel surface tethered with a combination of collagen type I, RGD peptides, and fibronectin. This surface was created by preparing a hydrogel surface-functionalized with the azide-active-ester linker, and then reacting the active esters with a solution of collagen, RGD peptides, and fibronectin molecules in a 1:1:1 molar ratio overnight. The cells were seeded on the surface in the way described above, and the photomicrograph was taken after 24 hours.

Early passage corneal fibroblast cells were seeded on collagen type I-modified microperforated PHEA substrates at a concentration of $1.0 \times 10^5$ cells/$cm^2$. Cells grew to confluence within 24 hours, as shown in FIG. 19F.

Implantation of Artificial Corneas

We have implanted collagen type I-modified PEG/PAA IPN optics intrastromally for periods of up to 2 months. New Zealand Red rabbits housed in the Animal Research Facility at Stanford University and weighing between 3.5 and 5.5 kg were anesthetized and prepared for surgery using a standard procedure. Before surgery, each rabbit was given an intramuscular injection of ketamine hydrochloride (40 mg/kg), xylazine hydrochloride (4 mg/kg) and glycopyrollate (0.02 mg/kg) with duration of action of 45 min. After this time period, half doses of ketamine hydrochloride (20 mg/kg) and xylazine hydrochloride (2 mg/kg) were administered at 30 min intervals as needed. Once the rabbits were placed under general anesthesia, proparacaine drops were applied to the corneas topically for additional local anesthesia. The sedated animals were then placed in the lateral decubitus position to facilitate surgery on the left eye. The lid margins and the surrounding periorbital area were cleaned with 10% iodine diluted 50:50 with balanced saline solution. Sterile surgical drapes were placed over the upper and lower eyelids of the left eye. Throughout the procedure, corneal drying was prevented by intermittent hydration with balanced saline solution. To facilitate proper suction prior to passage of the microkeratome, the rabbit's eye was slightly proptosed. The handle tip of a sterile, disposable scalpel was inserted into the temporal aspect of the lower conjunctival fornix. Using a delicate scooping motion with manual counter-pressure at the 12 o'clock position, the entire globe was proptosed slightly out of the orbit. Proptosis was then maintained by tying a 0-silk suture posteriorly to the equator of the globe. Placement of the hydrogel underneath the epithelial cell layer was achieved by creation of a LASIK flap using a Bausch & Lomb Hansatome microkeratome. Briefly, the 8.5 mm suction ring of the Hansatome apparatus was positioned to achieve adequate vacuum pressure, and then a 160-micrometer stromal flap was created using the microkeratome. The flap was lifted using a LASIK flap spatula, and a sterilized, 3.5 mm diameter hydrogel disc (100 μm thick) was placed onto the stromal bed. The flap was replaced and then sutured to the underlying stroma. Finally, a tarsorraphy (sutured lidclosure) was performed to reduce the chance of implant extrusion. Neomycin, Polymyxin B, and Dexamethasone combination drops were administered three times daily for 10 days post-operatively. Sutures for the cornea flap and eyelids were removed after 7 days.

Figure 20:
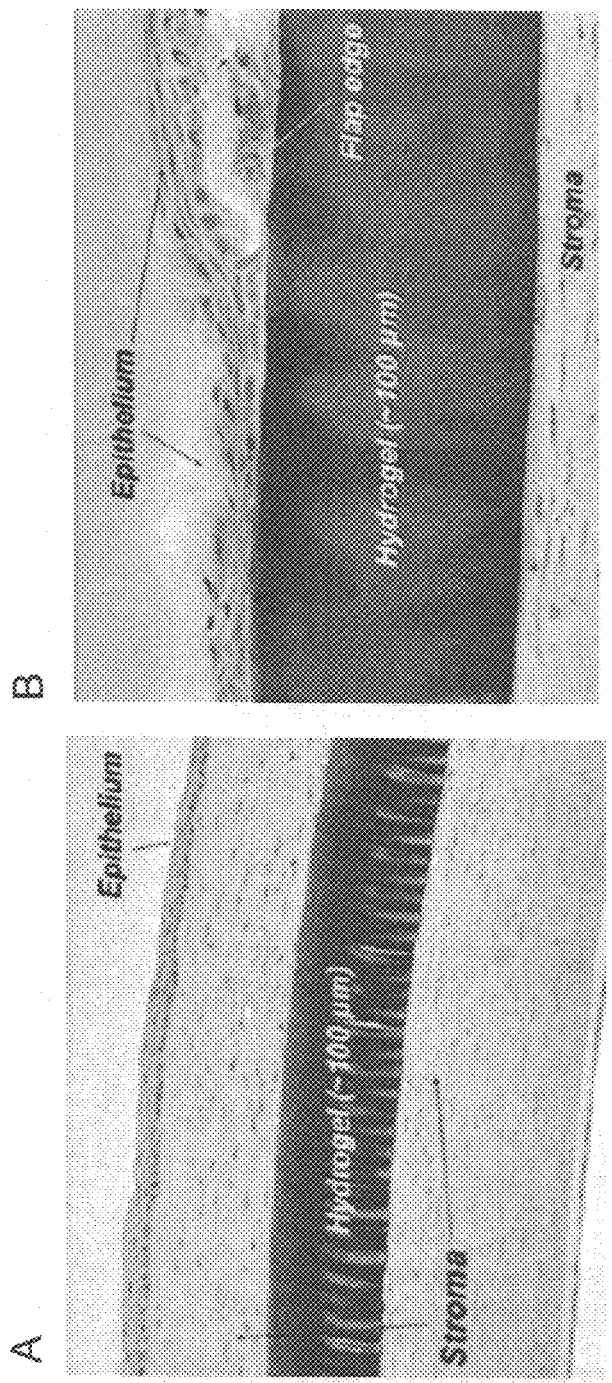
FIG. 20 shows examples of tissue integration of an implanted artificial cornea according to the present invention.

In preliminary studies, the implants were nearly indistinguishable from the surrounding stroma. During a two-week study, collagen type I surface modified PEG/PAA optics (~100 μm thick, 3.5 mm diameter) were implanted into 8 rabbits to assess the biocompatibility and nutrient permeability of the complete central optic prototype material. The implants were well-tolerated, with no signs of inflammation, epithelial ulceration, or opacification. In one of eight rabbits, the implant extruded due to mechanical factors associated with improper positioning of the optic. Clinical and histological evidence of epithelial and stromal health in these short-term studies demonstrates that the PEG/PAA IPN optics are biocompatible and can facilitate adequate nutrient transport to an overlying epithelium. FIG. 20A shows a histological section demonstrating healthy epithelial growth anterior to a PEG/PAA IPN hydrogel in a rabbit cornea after 14 days.

We have also studied the central optic's capacity to support surface epithelialization in live rabbit corneas. In our study, we implanted 3.5 mm diameter collagen type I-modified PEG/PAA optics into rabbit corneas using the following surgical techniques. A modified corneal onlay procedure was used to implant the PEG/PAA IPN optics. Animals were anesthetized, draped in a sterile fashion, and prepped as described above. Similarly, a LASIK flap was created in the left eye using the Hansotome microkeratome. Once the flap was created, a central hole in the flap was created by the following technique. The flap was lifted using a LASIK flap spatula. A flat metal spatula was then placed under the lifted flap to act as a foundation upon which a 1.5 mm diameter hole was created using a sterile skin biopsy punch. The attached edges were cut using vannas scissors. A 3.5 mm hydrogel button was placed over the stromal bed. The flap was then replaced such that the 1.5 mm flap hole laid over the center of the hydrogel button and was sutured down as described above. The 1 mm rim of stromal tissue was able to secure the implant within the cornea, while the central hole provided an area on the polymer onto which the surrounding epithelium could adhere and migrate. The migration and proliferation of epithelial cells across the polymer surface was evaluated using fluorescein dye to reveal non-epithelialized regions. Wound closure was determined by the lack of fluorescein staining at the end of postoperative week 2 (not shown). FIG. 20B shows histological evidence of multilayered cellular overgrowth on the optic after 14 days in vivo.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A material, comprising:
  a) an interpenetrating polymer network hydrogel, wherein said interpenetrating polymer network hydrogel comprises:
    i) a first hydrophilic network, wherein said first hydrophilic network is an entangled network of self-linked hydrophilic telechelic macromonomers covalently bonded to themselves or other of said macromonomers in said first network, wherein each of said hydrophilic telechelic macromonomers is a poly(ethylene) glycol (PEG) diacrylate or poly(ethylene) glycol (PEG) dimethacrylate based telechelic macromonomer;
    ii) wherein said first entangled hydrophilic network is interpenetrated with a second hydrophilic network, wherein said second network is a network of crosslinked poly(acrylic) acid; and
  b) biomolecules covalently linked to said interpenetrating polymer network hydrogel.

2. The material as set forth in claim 1, further comprising corneal epithelial cells or cornea-derived cells adhered to said biomolecules.

3. The material as set forth in claim 1, wherein said biomolecules are at least one of proteins, polypeptides, amino acids, carbohydrates, or nucleic acids.

4. The material as set forth in claim 1, wherein said biomolecules are at least one of cell adhesion molecules, immunoglobulins, or growth factors.

5. The material as set forth in claim 1, wherein said biomolecules are at least one of biomolecules found in the cornea, aqueous humor, cornea and aqueous humor or derivatives thereof.

6. The material as set forth in claim 1, wherein said first network comprises at least about 50% by dry weight of the reaction product of said telechelic macromonomer.

7. The material as set forth in claim 1, wherein said hydrophilic telechelic macromonomer has a molecular weight between about 575 Da and about 20,000 Da.

8. The material as set forth in claim 1, wherein at least one surface of said material is modified with a layer of poly (ethylene) glycol (PEG) macromonomers, polymerized PEG macromonomers, polymerized PEG diacrylate, or polymerized PEG dimethacrylate.

9. The material as set forth in claim 1, wherein said first network further comprises a hydrophilic monomer grafted onto said first network.

10. The material as set forth in claim 9, wherein said grafted hydrophilic monomer is acrylic acid, acrylamide, hydroxyethyl acrylamide, N-isopropylacrylamide, methacrylic acid, 2-acrylamido-2-methylpropanesulfonic acid, 2-hydroxyethyl methacrylate, 2-hydroxyethyl acrylate or derivatives thereof.

11. The material as set forth in claim 1, wherein said second network further comprises a hydrophilic telechelic macromonomer grafted onto said second network.

12. The material as set forth in claim 11, wherein said grafted hydrophilic telechelic macromonomer is PEG diacrylate or PEG dimethacrylate.

13. The material as set forth in claim 1, wherein said material has a tensile strength of at least about 1 MPa.

14. The material as set forth in claim 1, wherein said material has a nutrient diffusion coefficient in the range of about $10^{-5}$ cm$^2$/sec to about $10^{-7}$ cm$^2$/sec.

15. The material as set forth in claim 1, wherein said material has an equilibrium water content of between about 70% and about 95%.

16. The material as set forth in claim 1, wherein said material is at least about 70% transparent.

17. A corneal prosthesis, comprising:
a) an interpenetrating polymer network hydrogel, wherein said interpenetrating polymer network hydrogel comprises:
    i) a first hydrophilic network, wherein said first hydrophilic network is an entangled network of self-linked hydrophilic telechelic macromonomers covalently bonded to themselves or other of said macromonomers in said first network, wherein each of said hydrophilic telechelic macromonomers is a poly(ethylene) glycol (PEG) diacrylate or poly(ethylene) glycol (PEG) dimethacrylate based telechelic macromonomer;
    ii) wherein said first entangled hydrophilic network is interpenetrated with a second hydrophilic network, wherein said second network is a network of crosslinked poly(acrylic) acid; and
b) biomolecules covalently linked to said interpenetrating polymer network hydrogel.

18. The corneal prosthesis as set forth in claim 17, further comprising corneal epithelial cells or cornea-derived cells adhered to said biomolecules.

19. The corneal prosthesis as set forth in claim 17, wherein said biomolecules are at least one of proteins, polypeptides, amino acids, carbohydrates, or nucleic acids.

20. The corneal prosthesis as set forth in claim 17, wherein said biomolecules are at least one of cell adhesion molecules, immunoglobulins, or growth factors.

21. The corneal prosthesis as set forth in claim 17, wherein said biomolecules are at least one of biomolecules found in the cornea, and aqueous humor or derivatives thereof.

22. The corneal prosthesis as set forth in claim 17, wherein said first network comprises at least about 50% by dry weight of the reaction product of said telechelic macromonomer.

23. The corneal prosthesis as set forth in claim 17, wherein said hydrophilic telechelic macromonomer has a molecular weight between about 575 Da and about 20,000 Da.

24. The corneal prosthesis as set forth in claim 17, wherein at least one surface of said artificial cornea is modified with a layer of poly(ethylene) glycol (PEG) macromonomers, polymerized PEG macromonomers, polymerized PEG diacrylate, or polymerized PEG dimethacrylate.

25. The corneal prosthesis as set forth in claim 17, wherein said first network further comprises a hydrophilic monomer grafted onto said first network.

26. The corneal prosthesis as set forth in claim 25, wherein said grafted hydrophilic monomer is acrylic acid, acrylamide, hydroxyethyl acrylamide, N-isopropylacrylamide, methacrylic acid, 2-acrylamido-2-methylpropanesulfonic acid, 2-hydroxyethyl methacrylate, 2-hydroxyethyl acrylate or derivatives thereof.

27. The corneal prosthesis as set forth in claim 17, wherein said second network further comprises a hydrophilic telechelic macromonomer grafted onto said second network.

28. The corneal prosthesis as set forth in claim 27, wherein said grafted hydrophilic telechelic macromonomer is PEG diacrylate or PEG dimethacrylate.

29. The corneal prosthesis as set forth in claim 17, wherein said artificial cornea has a tensile strength of at least about 1 MPa.

30. The corneal prosthesis as set forth in claim 17, wherein said artificial cornea has a nutrient diffusion coefficient in the range of about $10^{-5}$ cm$^2$/sec to about $10^{-7}$ cm$^2$/sec.

31. The corneal prosthesis as set forth in claim 17, wherein said artificial cornea has an equilibrium water content of between about 70% and about 95%.

32. The corneal prosthesis as set forth in claim 17, wherein said artificial cornea is at least about 70% transparent.

33. The corneal prosthesis as set forth in claim 17, further comprising a skirt peripheral to said interpenetrating polymer network hydrogel, wherein said skirt is hydrophilic, contains pores, is hydrogel-based and is biocompatible.

34. The corneal prosthesis as set forth in claim 33, wherein said skirt comprises an interpenetrating polymer network hydrogel, wherein said interpenetrating polymer network hydrogel comprises:
a) a first hydrophilic network, wherein said first hydrophilic network is an entangled network of self-linked hydrophilic telechelic macromonomers covalently bonded to themselves or other of said macromonomers in said first network, wherein each of said hydrophilic telechelic macromonomers is a poly(ethylene) glycol (PEG) diacrylate or poly(ethylene) glycol (PEG) dimethacrylate based telechelic macromonomer; and
b) whereby said first entangled hydrophilic network is interpenetrated with a second hydrophilic network, wherein said second network is a network of crosslinked poly(acrylic) acid.

35. The corneal prosthesis as set forth in claim 33, wherein said skirt comprises poly(2-hydroxyethyl acrylate).

36. The corneal prosthesis as set forth in claim 33, wherein said artificial cornea further comprises biomolecules covalently linked to said skirt.

37. The corneal prosthesis as set forth in claim 33, wherein said pores have a diameter between about 20 μm and about 200 μm.

38. The material as set forth in claim 1, wherein the molar ratio between said first network and said second network is about 1:1 to about 1:5000.

39. The material as set forth in claim 1, wherein the weight ratio between said first network and said second network is about 10:1 to about 1:10.

40. The corneal prosthesis as set forth in claim 17, wherein the molar ratio between said first network and said second network is about 1:1 to about 1:5000.

41. The corneal prosthesis as set forth in claim 17, wherein the weight ratio between said first network and said second network is about 10:1 to about 1:10.

* * * * *